(12) United States Patent
Acemoglu et al.

(10) Patent No.: US 8,987,413 B2
(45) Date of Patent: Mar. 24, 2015

(54) ALDEHYDE ACETAL BASED PROCESSES FOR THE MANUFACTURE OF MACROCYCLIC DEPSIPEPTIDES AND NEW INTERMEDIATES

(71) Applicants: Murat Acemoglu, Basel (CH); Heribert Hellstern, Heitersheim (DE); Bernard Riss, Huningue (FR); Christian Sprecher, Rafz (CH)

(72) Inventors: Murat Acemoglu, Basel (CH); Heribert Hellstern, Heitersheim (DE); Bernard Riss, Huningue (FR); Christian Sprecher, Rafz (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/042,950

(22) Filed: Oct. 1, 2013

(65) Prior Publication Data

US 2014/0100353 A1   Apr. 10, 2014

Related U.S. Application Data

(60) Provisional application No. 61/711,282, filed on Oct. 9, 2012.

(51) Int. Cl.
| | | |
|---|---|---|
| A61K 38/12 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 11/02 | (2006.01) | |
| C07D 317/30 | (2006.01) | |
| C07C 229/22 | (2006.01) | |
| C07K 7/06 | (2006.01) | |

(52) U.S. Cl.
CPC .............. *C07K 11/02* (2013.01); *C07D 317/30* (2013.01); *C07C 229/22* (2013.01); *C07K 7/06* (2013.01)
USPC .......................................................... 530/317

(58) Field of Classification Search
CPC ................................ A61K 38/00; C07K 11/02
See application file for complete search history.

(56) References Cited

U.S. PATENT DOCUMENTS

| | | | |
|---|---|---|---|
| 5,595,756 | A | 1/1997 | Bally et al. |
| 6,630,569 | B1 | 10/2003 | Jeschke et al. |
| 8,178,650 | B2 | 5/2012 | Krastel et al. |
| 8,415,305 | B2 | 4/2013 | Krastel et al. |
| 8,614,289 | B2 | 12/2013 | Acemoglu et al. |
| 8,680,054 | B2 | 3/2014 | Haug |
| 2004/0110228 | A1 | 6/2004 | McAlpine et al. |
| 2005/0014684 | A1 | 1/2005 | Palomera et al. |
| 2009/0036487 | A1 | 2/2009 | Field et al. |
| 2009/0186042 | A1 | 7/2009 | Johnston et al. |
| 2010/0209376 | A1 | 8/2010 | Richters et al. |
| 2012/0064136 | A1 | 3/2012 | Baker et al. |
| 2013/0017226 | A1 | 1/2013 | Park et al. |
| 2014/0100355 | A1 | 4/2014 | Acemoglu et al. |

FOREIGN PATENT DOCUMENTS

| | | |
|---|---|---|
| EP | 0 052 200 A1 | 9/1981 |
| JP | 2000154198 A | 6/2000 |
| WO | 9534558 A1 | 12/1995 |
| WO | 2004108139 A2 | 12/2004 |
| WO | 2005075667 A1 | 8/2005 |
| WO | 2011003858 A2 | 1/2011 |
| WO | 2012035468 A2 | 3/2012 |
| WO | 2012103035 A1 | 8/2012 |
| WO | 2012103038 A2 | 8/2012 |

OTHER PUBLICATIONS

Elert et al, 'Cyanopeptolin 954, a Chlorine-Containing Chymotrypsin Inhibitor of *Microcystis aeruginosa* NIVA Cya 43', J Nat Prod 68(9): 1324-1327 (2005).

Yokokawa et. al., 'Synthetic studies towards 3-Amino-6-hydroxy-2-piperidone (Ahp)-Containing Cyclic Depsipeptides', Peptide Science 38:33-36 (2001).

Johannesson et al., "Angiotensin II Analogues Encompassing 5, 9- and 5,10-Fused ThiazabicycloalkaneTripeptide Mimetics", J. Med. Chem 42(22):4524-4537 (Nov. 1, 1999).

Yokokawa et. al., Synthetic studies of micropeptin T-20, a novel 3-amino-6-hydroxy-2-piperidone (AHP)-containing cyclic depsipeptide, Tetrahedron Letters 42(34): 5903-5908 (2001).

(Continued)

*Primary Examiner* — Marcela M Cordero Garcia
*Assistant Examiner* — Kaipeen Yang
(74) *Attorney, Agent, or Firm* — Sophie Binet Cross

(57) ABSTRACT

The invention relates to a method or process for the chemical manufacture of depsipeptides of the formula I employing an aldehyde acetal intermediate,

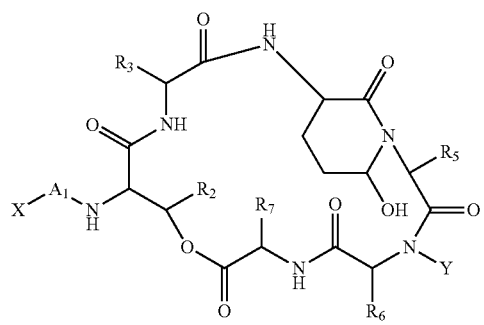

wherein the symbols have the meaning defined in the description, to new intermediates and their manufacture, as well as related invention embodiments.

15 Claims, No Drawings

(56) References Cited

OTHER PUBLICATIONS

Yokokawa et. al., Synthetic studies of the cyclic depsipeptides bearing the 3-amino-6-hydroxy-2-piperidinone (Ahp) unit. Total synthesis of the proposed structure of micropeptin T-20, Tetrahedron 61(6):1459-1480 (2005).

Itau et al, "Oscillapeptins A to F, Serine Protease Inhibitors from the Three Strains of *Oscillatoria agardhii*," Tetrahedron 55(22):6871-6882 (1999).

Namikoshi et al., "Bioactive compounds produced by cyanobacteria," J Ind Microbiol Biotech 17(5-6): 373-384 (1996).

McDonough et al, "New Structural Insights into the Inhibition of Serine Proteases by Cyclic Peptides from Bacteria," Chem & Biol 10(10):898-900 (Oct. 2003).

Franzke et al, "Antileukoprotease Inhibits Stratum Corneum Chymotryptic Enzyme," J Biol Chem 271(36):21886-21890 (1996).

Harada et al, "Co-production of Microcystins and Aeruginopeptins by Natural Cyanobactieral Bloom," Environ Toxicol 16:298-305 (2001).

Grach et al, "Protease inhibitors from a Slovenian Lake Bled toxic waterbloom of the cyanobacterium Planktothrix rubescens," Tetrahedron 59(42):8329-8336 (2003).

Matern et al., "Binding Structure of Elastaste Inhibitor Scyptolin A," Chemistry & Biology 10:997-1001 (Oct. 2003).

Nakanishi et al, "Structure of Porcine Pancreatic Elastase Compled with FR901277, a Novel Macrocyclic Inhibitor of Elastases, at 1.6 A Resolution," Biopolymers 53(5):434-445 (2000).

Hansson et al., "Epidermal Overexpression of Stratum Corneum Chymotryptic Enzyme in Mice: A Model for Chronic Itchy Dermatitis," J. Invest. Dermatol. 118(3):444-449 (2002).

Hachem et al.; "Serine Protease Activity and Residual LEKTI Expression Determine Phenotype in Netherton Syndrome"; Journal of Investigative Dermatology, 126:1609-1621 (2006).

Hiemstra, "Novel roles of protease inhibitors in infection and inflammation," Biochem Soc Trans 30(2): 116-120 (2002).

Kunze et al, << Chondramides A-D, New Antifunal and Cytostatic Depsipeptides from Chondromyces crocatus, << J Antibiot 48(11):1262-1266 (Nov. 1995).

Ekholm and Egelrud "Stratum corneum chymotryptic enzyme in psoriasis," Arch Dermatol Res 291(4): 195-200 (1999).

Vasilopoulos et al. "Genetic Association Between an AACC Insertion in the 3'UTR of the Stratum Corneum Chymotryptic Enzyme Gene and Atopic Dermatitis," J. Invest. Dermatol. 123:62-66 (2004).

Banker et al, "Inhibitors of Serine Protease from a Waterbloom of the Cyanobacterium *Microcystis* sp.," Tetrahedron 55(35): 10835-10844 (1999).

Bonjouklian et al., "A90720A, A Serine Protease Inhibitor Isolated From a Terrestrial Blue-Green Alga Microchaete loktakensis," Tetrahedron 52(2):395-404 (1996).

Reshef and Carmeli, "Protease inhibitors from a water bloom of the cyanobacterium *Microcystis aeruginosa*," Tetrahedron 57(14):2885-2894 (2001).

Fairlie et al., "Conformational Selection of Inhibitors and Substrates by Proteolytic Enzymes: Implications for Drug Design and Polypeptide Processing," J Med Chem 43(7): 1271-1281 (2000).

Matthew et al., << Lyngbyastatin 4, a Dolastatin 13 Analogue with Elastase and Chymotrypsin Activity from the Marine *Cyanobacterium lyngbya* confervoides, J Nat Prod 70(1):124-127 (2007).

Radau G., "Serine proteases inhibiting cyanopeptides," Pharmazie 55(8):555-560 (2000).

Egelrud, Torbjorn, "Purification and Preliminary Characterization of Stratum Corneum Chymotryptic Enzyme: A Proteinase That May Be Involved in Desquamation," J Invest Dermatol 101(2):200-204 (1993).

Tsukamoto et.al.,MicrocystilideA: A Novel Cell-Differentiation-Prompting Depsipeptide from *Microcystis aeruginosa* NO-15-1840, J. Am. Chem. Soc. 115:11046-11047 (1993).

Harada et al., Application of D,L-FDLA Derivatization to Determine of Absolute Configuration of Constituent Amino Acids in Peptide by Advanced Marfey's Method,Tetrahedron Letters 37(17):3001-3004 (1996).

Fujii et al., "Development of a Method for Determining the Absolute Configuration of Constituent Amino Acids in Peptides Using LC/MS," Tennen Yuki Kagobutsu Toronkai Koen Yoshishu 39:223-228 (1997).

Cochrane et. al., 'Total Synthesis and Assignment of the Side Chain Stereochemistry of LI-F04a: An Antimicrobial Cyclic Depsipeptide', Organic Letters 12(15):3394-3397 (2010).

Seo and Lim, 'Total Synthesis of Halicylindramide A,' Journal of Organic Chemistry 74:906-909 (2009).

Okumura et. al., 'Homotyrosine-Containing Cyanopeptolins 880 and 960 and Anabaenopeptins 908 and 915 from *Planktothrix agardhii* CYA 126/8', J Nat Prod 72:172-176 (2009).

Ishida et. al., Micropeptins 88-A to 88-F, Chymotrypsin Inhibitors from the Cyanobacterium *Microcystis aeruginosa* (NIES-88), Tetrahedron 54(21):5545-5556 (1998).

Zainuddin et. al., 'Cyclic Depsipeptides, Ichthyopeptins A and B, from Microcystis ichthyoblabe', J. Nat. Prod 70:1084-1088 (2007).

Olsen et al.,Synthesis of Nalpha, Nbeta-protected Ndelta-Hydroxy-L-ornitine from L-Glutamic Acid, J. Org. Chem. 49:3527-3534 (1984).

Yoshiya et al., "O-Acyl isopeptide method" for peptide synthesis: synthesis of forty kinds of "O-acyl isodipeptide unit" Boc-Ser/Thr(Fmoc-Xaa)-OH, Organic & Biomolecular Chemistry 5:1720-1730 (2007).

Stolze et al., "Solid phase total synthesis of the 3-amino-6-hydroxy-2-piperidone (Ahp) cyclodepsipeptide and protease inhibitor Symplocamide A", Chemical Communications 46:8857-8859 (2010).

Stolze et al., "Development of a Solid-Phase Approach to the Natural Product Class of Ahp-Containing Cyclodepsipeptides", European Journal of Organic Chemistry 2012:1616-1625 (2012).

Stawikowski and Cudic, "A novel strategy for the solid-phase synthesis of cyclic lipodepsipeptides", Tetrahedron Letters 47:8587-8590 (2006).

Bourel-Bonnet et al., "Solid-Phase Total Synthesis of Kahalalide A and Related Analogues", Journal of Medicinal Chemistry 48:1330-1335 (2005).

Lautenschläger et al., "Fettstoffe—die Basis der Hautpflege" Kosmetische Praxis 6:6-8 (2003).

Pena et. al., "Structural Rheology of a Model Ointment", Pharmaceutical Research 11(6)875-881 (1994).

Bos et. al., "The 500 Dalton rule for the skin penetration of chemical compounds and drugs," Experimental Dermatology 9:165-169 (2000).

Benson et. al. "Proteins and Peptides: Strategies for Delivery to and Across the Skin", Journal of Pharmaceutical Sciences, vol. 97, 3591-3610 (2008).

Berendsen, Herman, "A Glimpse of the Holy Grail?" Science 282:642-643 (Oct. 23, 1998).

Rudinger J, "Characteristics of the amino acids as components of a peptide hormone sequence," Peptide Hormones, JA Parsons Ed., 1-7 (1976).

Schinzel and Drueckes, "The phosphate recognition site of *Escherichia coli* matodextrin phosphorylase," FEBS 286(1, 2):125-128 (Jul. 1991).

Voet et al, Biochemistry, Second Edition, John Wiley & Sons, Inc, 1995, 235-241.

Ngo et al., "Computational Complexity, Protein Structure Prediction and the Levinthal Paradox," The Protein Folding Problem and Tertiary Structure Prediction, K. Merc Jr. and S. Le Grand Edition, 1994, 491-495.

Bradley and Barrick, "Limits of Cooperativity in a Structurally Modular Protein: Response of the Notch Ankyrin Domain to Analogous Alanine Substitutions in Each Repeat," J. Mol. Biol. 324:373-386 (2002).

Sporn and Suh, "Chemoprevention of cancer," Carcinogenesis 21(3):525-530 (2000).

Auerbach et al., "Angiogenesis assays, Problems and pitfalls," Cancer and Metastasis Reviews 19:167-172 (2000).

(56) References Cited

OTHER PUBLICATIONS

Gura, T., "Systems for Identifying New Drugs Are Often Faulty," Science 278(5340):1041-1042 (Nov. 7, 1997).
Jain, Rakesh K., "Barriers to Drug Delivery in Solid Tumors," Scientific American 58-65 (Jul. 1994).
Pearce et al., "Failure modes in anticancer drug discovery and development," Cancer Drug Design and Discovery 424-435 (2008).
Custom Peptide Synthesis, "Designing Custom Peptides," SIGMA Genosys, 1-2, (Dec. 16, 2004).
Yokokawa et. al., 'Total synthesis of sonamide A, an Ahp (3-amino-6-hydroxy-2-piperidone)-containing cyclic depsipeptide, Tetrahedron Letters 43(48):8673-8677 (2002).
Matsuda et al., Tennen Yuki Kagobutsu Toronkai Koen Yoshishu 35:654-661. (1993).
Dark, Graham, The On-Line Medical Dictionary, World-Wide Web URL: http://cancerweb.nc..ac.uk/omd/index.html, published at the Dept. of Medical Oncology, University of Newcastle upon Tyne, copyright:1997-2003, pp. 1-2.
Residue Definition, http://dictionary.reference.com/browse/residue, (2009), pp. 1-4.

ALDEHYDE ACETAL BASED PROCESSES FOR THE MANUFACTURE OF MACROCYCLIC DEPSIPEPTIDES AND NEW INTERMEDIATES

This application claims benefit under 35 U.S.C. §119(e) of U.S. Provisional Application No. 61/711,282, filed Oct. 9, 2012; the content of which is incorporated herein by reference in their entirety.

SUMMARY OF THE INVENTION

The invention relates to a method or process for the manufacture of macrocyclic depsipeptides, to new intermediates and their manufacture, as well as related invention embodiments.

BACKGROUND OF THE INVENTION

Cyclic depsipeptides have numerous uses in pharmacology. As an example, the depsipeptides disclosed in WO2009/024527 are useful for treatment of various diseases. For example, the compound of formula II mentioned in WO2009/024527 is useful for the treatment and prevention of inflammatory and/or hyperpoliferative and pruritic skin diseases such as atopic dermatitis, psoriasis, pustular psoriasis, rosacea, keloids, hypertrophic scars, acne, Netherton's syndrome or other pruritic dermatoses such as prurigo nodularis, unspecified itch of the elderly as well as other diseases with epithelial barrier dysfunction such as aged skin.

Nostopeptin BN920, formerly isolated from the cyanobacterium Nostoc, was isolated also from Microcystis. Nostopeptin BN920 inhibited chymotrypsin with an IC50 value of 31 nM (see J. Nat. Prod. 68(9), 1324-7 (2005)).

These compounds can be produced by fermentation (using chondromyces croactus, myxobacteria) along with other depsipeptides comprising the so-called ahp-substructure (ahp: 3-amino-6-hydroxy-piperidin-2-one) and the corresponding dehydro-ahp substructure (dehydro-ahp: 3-amino-3,4-dihydro-1H-pyridin-2-one), also called "dehydrate" herein, respectively. Therefore, the yield of fermentation with regard to any single of these compounds is rather low.

Hitherto, the synthesis of such compounds was based on solution chemistry approaches or in copending PCT application No. PCT/IB2012/051977 by a combination of solid phase and solution peptide chemistry.

A critical step is the formation of the ahp-substructure. This, according to published prior art, is mainly formed by oxidation of the open chain precursor amino acid 2-amino-5-hydroxy-pentanoic acid in the closed macrolactone ring by oxidative treatment via a labile aldehyde intermediate (see e.g. Yokohama et al., Tetrahedron 61 (2005), pp. 1459-80, compound 23; Yokohama et al., Pept. Sci. 38 (2002). Pp. 33-36; and Yokohama et al., Tetrahedron Lett. 42 (2001), 5903-8).

The aldehyde is too instable to be isolated. Therefore its direct use and synthesis are not recommended.

Aldehyde derivatives, such as acetals, are also known to be instable, in particular in the case where acetal and (especially free) carboxylic acid functions are present simultaneously or under (even only slightly) acidic conditions.

There is a need to find higher yielding processes and processes that are easier in handling for the manufacture of macrolactone ring systems comprising ahp moieties.

It has now been found that it is possible to replace the precursor with the 2-amino-5-hydroxypentanoic acid building block and use its 5-oxo-analogue in acetal form instead.

The present invention thus relates to processes or methods that allow obtaining such cyclic depsipeptides with increased yield and/or in good purity and with a lower number of steps.

In view of the many risks, such as racemization, tautomerization and the like, in the synthesis of a complex molecule with many possible isomers, it has been possible to find a manufacturing process, preferably comprising a mixture of solid phase peptide synthesis and reactions in solution, that allows to produce cyclic depsipeptides of formula I in good yield and/or with the required stereoisomerical purity, especially both, and that avoids the steps of oxidation of a hydroxyl group in the precursor molecule. It is possible to reduce the amount of by-products, and even to improve yield, by converting such by-products, especially the dehydro-ahp substructure and/or an analogue of the desired ahp-comprising products with a five-ring instead of the ahp, into the desired final products. No synthesis has so far come to our attention making use of solid phase peptide synthesis in this field. In addition, the elimination of the oxidation step allows using N-Me-Tyosine or analogues instead of the protected variants such as t-butyl-ethers or analogues thereof which are expensive and difficult to prepare.

(i/a) In a first embodiment, the invention relates to a method or process for the preparation of a cyclic depsipeptide compound of the formula I,

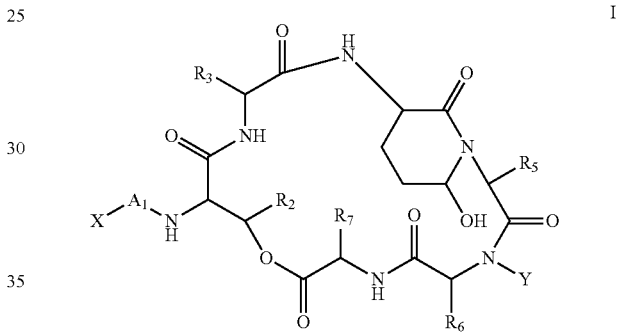

especially of the formula IA

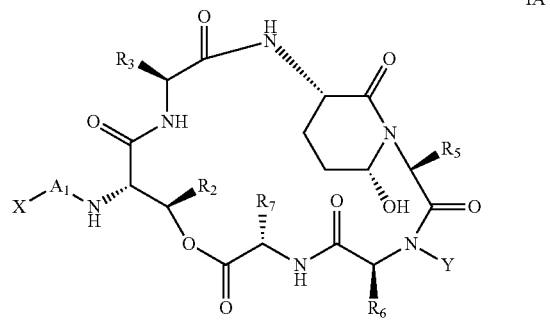

wherein
$A_1$ is a bivalent moiety of an amino acid with a terminal carboxy or carbamoyl group, especially asparagine or glutamine, and is bound at its right hand side in formula I via a carbonyl (preferably the carbonyl of an α-carboxyl group thereof) to the rest of the molecule; or is $C_{1-8}$-alkanoyl or phosphorylated hydroxy-$C_{1-8}$-alkanoyl;
X is bound via an N of $A_1$ and is acyl, or is absent if $A_1$ is $C_{1-8}$-alkanoyl or phosphorylated hydroxy-$C_{1-8}$-alkanoyl;
$R_2$ is $C_{1-8}$-alkyl, especially methyl;
$R_3$ is the side chain of an amino acid, especially of leucine, isoleucine or valine;
$R_5$ is the side chain of an amino acid, preferably of phenylalanine, leucine, isoleucine or valine;

$R_6$ is the side chain of a hydroxy amino acid, especially of tyrosine;

$R_7$ is the side chain of an amino acid, preferably of the amino acid leucine, isoleucine or valine; and Y is hydrogen or $C_{1-8}$-alkyl;

or a salt thereof, said method comprising deprotecting a compound of the formula II

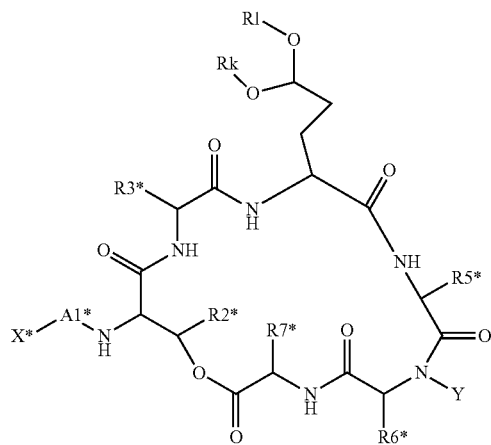

especially of the formula IIA

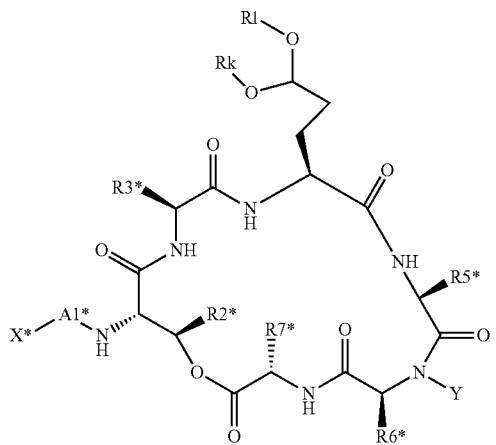

wherein the aldehyde protecting group(s) Rk and Rl are independently of each other unsubstituted or substituted alkyl or together with the two binding O atoms and the carbon atom to which the two O atoms are bound form a ring that is unsubstituted or substituted (Rk and Rl then preferably forming an unsubstituted or substituted alkylene bridge, especially unsubstituted or substituted ethylen, such as —$CH_2$—$CH_2$— or —$CH_2$—$CH_2$—$CH_2$—), Y is as defined for a compound of the formula I and $X^*$, $A_1^*$, $R_2^*$, $R_3^*$, $R_5^*$, $R_6^*$, and $R_7^*$ correspond to X, $A_1$, $R_2$, $R_3$, $R_5$, $R_6$, and $R_7$ in formula I, respectively, but with the proviso that reactive functional groups on these moieties (such as amino, imino, hydroxy, carboxy, sulfhydryl, amidino, guanidino, O-phosphono (—O—P(=O)(OH)$_2$) are present in protected form at least if they could participate in undesired side reactions, to result in a compound of the formula I, especially IA;

and, if desired, converting a free compound of the formula I, or especially IA, into a salt, a salt of a compound of the formula I into a different salt of a compound of the formula I, or especially IA, or into the free compound of the formula I, or especially IA, and/or converting a dehydrate analogue and/or five ring analogue of a compound of the formula I, or especially IA, into the corresponding compound of the formula I, or especially IA.

(ii/a) A further embodiment of the invention refers to the method or process described above, in addition comprising manufacturing the compound of the formula II or especially IIA by a combination of Solid Phase Peptide Synthesis (especially for synthesis of the precursor of formula III or III* or especially IIIA or IIIA* given below, and Solution Phase synthesis (especially from the compounds just mentioned to the final product) from the corresponding starting amino acids and side chain precursors.

(i/b) Yet a further embodiment of the invention relates to a method or process as described above, further comprising, for the synthesis of a compound of the formula II above, cyclization under lactamization (macrolactamization) of a linear precursor peptide of the compound of the formula II or especially of the formula IIA, carrying an N-terminal amino group and a C-terminal carboxy group, under reaction conditions that allow for the formation of an amide bond from said amino and said carboxy group, preferably using Solution Phase chemistry.

(ii/b) A further embodiment of the invention relates to the method or process according to the preceding paragraph (i/b), where the linear precursor peptide is of the formula III,

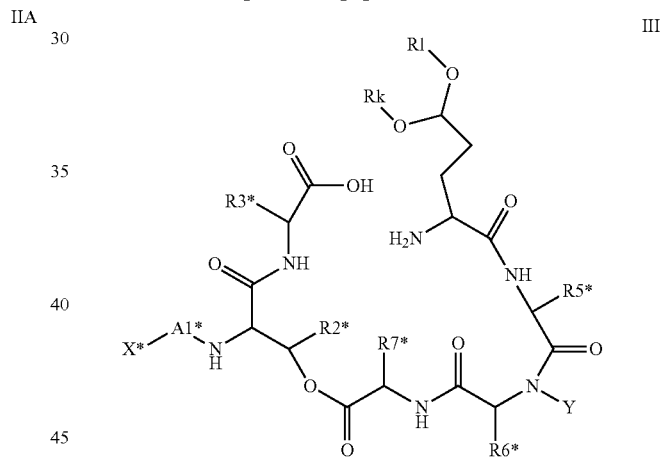

especially IIIA,

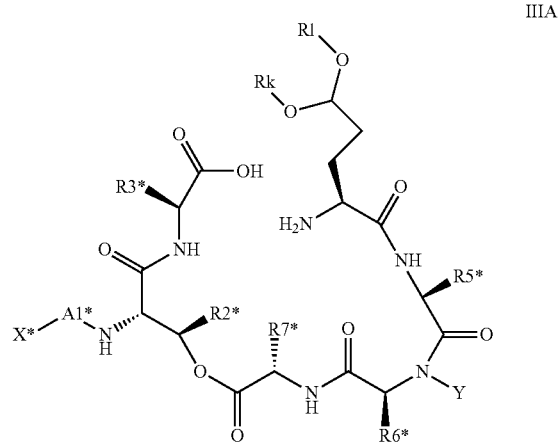

wherein Rk, Rl, X*, A$_1$*, R$_2$*, R$_3$*, R$_5$*, R$_6$* and R$_7$* are as defined for a compound of the formula II above, which can be obtained directly from solid phase peptide synthesis (e.g. as described under step (iii/b) or by deprotection from the corresponding compound of the formula III*,

III*

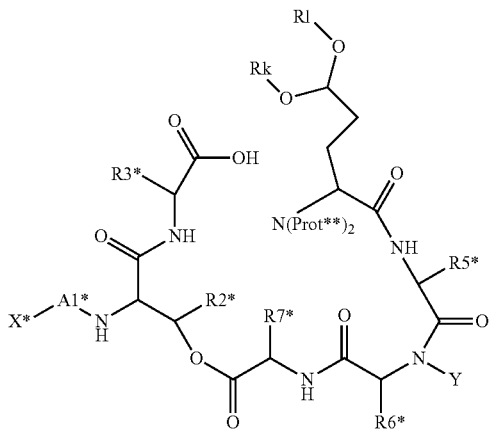

especially IIIA*,

IIIA*

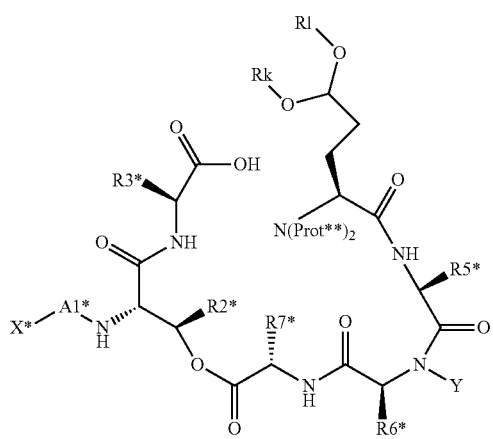

wherein Rk, Rl, X*, A$_1$*, R$_2$*, R$_3$*, R$_5$*, R$_6$* and R$_7$* are as defined for a compound of the formula II above and wherein each of the Prot** moieties is a protecting group that can preferably must) be removed under conditions different from those of the cleavage under (iii/b), especially each is an arylalkyl amino protecting group, as defined for a compound of the formula IV, by deprotecting the protected amino group.

(iii/b) Another embodiment refers to the method or process according to the preceding paragraph (ii/b), further comprising, for the synthesis of the compound of the formula III or especially IIIA, or of a compound of the formula III*, especially IIIA*, cleaving a compound of the formula IV,

IV

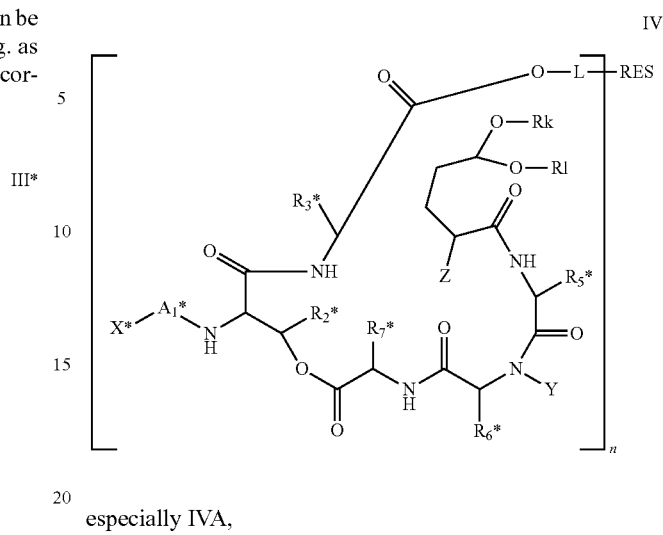

especially IVA,

IVA

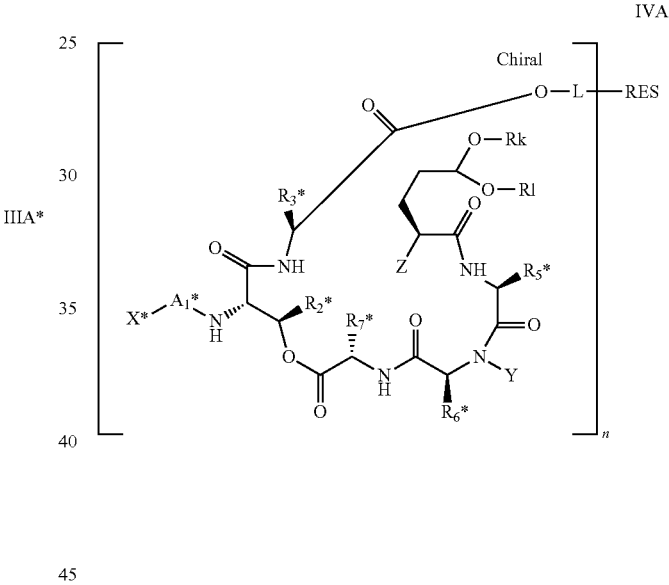

wherein Rk, Rl, X*, A$_1$*, R$_2$*, R$_3$*, R$_6$*, R$_6$* and R$_7$* are as defined for a compound of the formula II above, L is a cleavable linker, RES is a solid resin, n is a natural number not including 0 and Z is a protected amino group either of the formula NHProt* wherein Prot* is a protecting group that is removed before or during the cleaving reaction or further subsequently to it [?] to yield a compound of the formula III, especially IIIA; or Z is a protected amino group of the formula N(Prot)$_2$ wherein each Prot is an amino protecting group that can (in particular can only) be removed under conditions different from those of the cleaving reaction, especially each is an arylalkyl amino protecting group, to yield the compound of the formula III*, especially IIIA*.

(iv/b) A further embodiment of the invention relates to the method or process according to the preceding paragraph (iii/b), further comprising, for the synthesis of the compound of the formula IV, especially IVA, coupling an amino acid of the formula V,

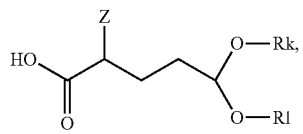

especially VA,

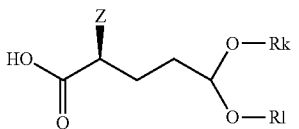

VA wherein Rk and Rl are as defined for a compound of the formula II above and Z is a protected amino group either of the formula NHProt* wherein Prot* is a protecting group that can be (and is) removed before or during the cleaving reaction under (iii/b) or further subsequently; or Z is a protected amino group of the formula N(Prot)₂ wherein each Prot is an amino protecting group that can be removed under conditions different to those of the cleaving reaction under (iii/b), especially each is an arylalkyl amino protecting group; or an activated derivative of said amino acid of the formula V or VA, with a compound of the formula VI,

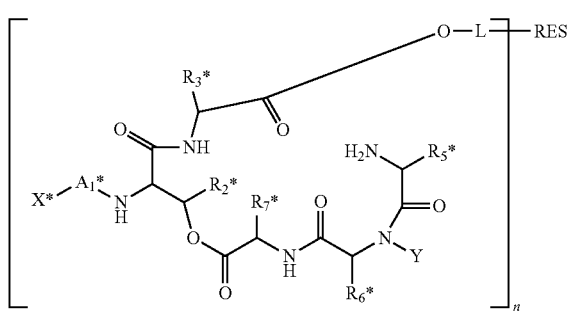

especially VIA,

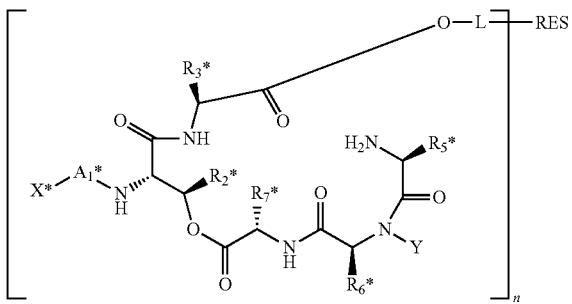

wherein X*, A₁*, R₂*, R₃*, R₅*, R₆* and R₇* are as defined for a compound of the formula II above, L is a cleavable linker, RES is a solid resin, and n is a natural number not including 0.

(v/b) Yet a further embodiment of the invention relates to the method or process according to the preceding paragraph (iv/b), further comprising, for the synthesis of the compound of the formula VI, especially VIA, coupling an amino acid of the formula VII

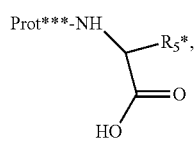

especially VIIA,

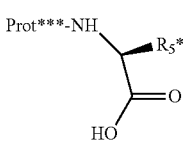

wherein R₅* is as defined for a compound of the formula II above and Prot*** is an amino protecting group that can be cleaved off selectively without affecting other protecting groups present and with the coupling product remaining on the resin, or a reactive derivative of said amino acid, with a compound of the formula VIII,

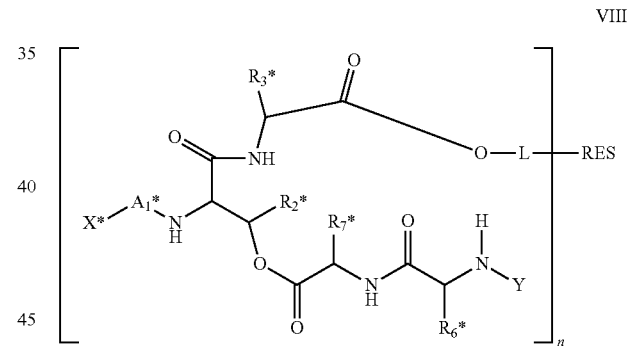

especially VIIIA

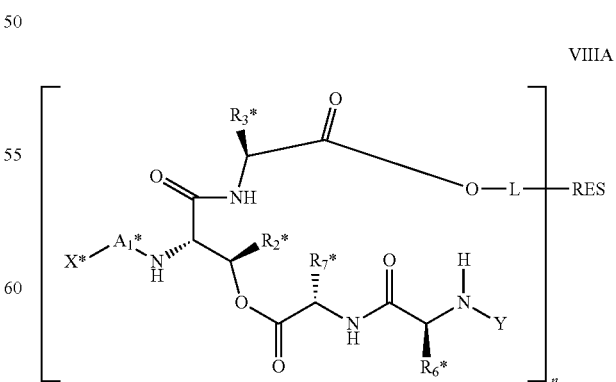

wherein X*, A₁*, R₂*, R₃*, R₆* and R₇* are as defined for a compound of the formula II above, L is a cleavable linker, RES is a solid resin, and n is a natural number not including 0, and removing the protecting group Prot***.

(vi/b) In yet a further embodiment, the invention relates to the method or process according to the preceding paragraph (v/b), further comprising, for the synthesis of the compound of the formula VIII, especially VIIIA, coupling an amino acid of the formula IX,

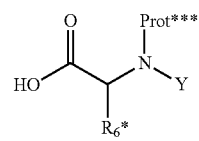

especially IXA

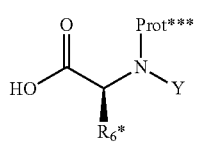

in which $R_6^*$ and Y are as defined for a compound of the formula II above and Prot*** is an amino protecting group that can be cleaved off selectively without affecting other protecting groups present and with the coupling product remaining on the resin, or a reactive derivative of said amino acid, with a compound of the formula X,

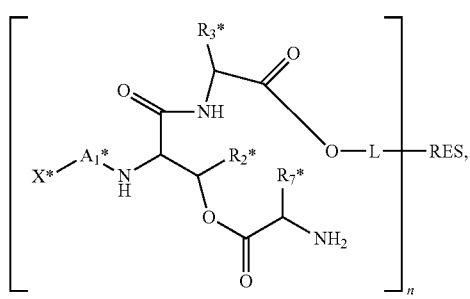

especially XA,

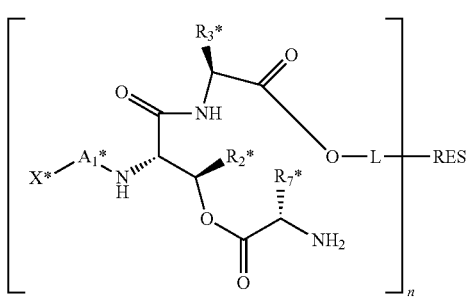

wherein $X^*$, $A_1^*$, $R_2^*$, $R_3^*$ and $R_7^*$ are as defined for a compound of the formula II above, L is a cleavable linker, RES is a solid resin, and n is a natural number not including 0, and removing the protecting group Prot***.

(vii/b) Another embodiment of the invention relates to the method or process according to the preceding paragraph (vi/b), further comprising, for the synthesis of a compound of the formula X, especially XA, reacting an amino acid of the formula XI,

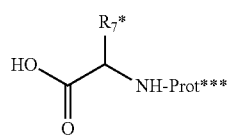

especially XIA,

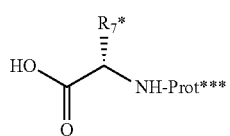

wherein Prot*** is an amino protecting group that can be cleaved off selectively without affecting other protecting groups present and with the product remaining on the resin, and $R_7^*$ is as defined for a compound of the formula II above, or a reactive derivative of said amino acid, with the hydroxyl group of a compound of the formula XII,

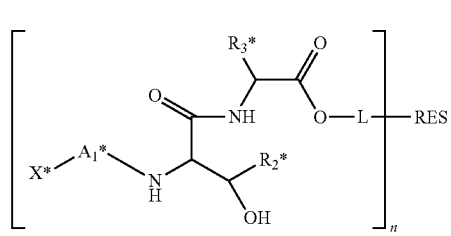

especially XIIA,

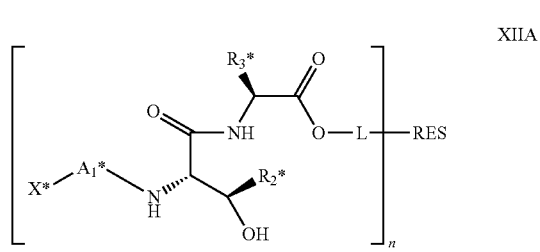

wherein $X^*$, $A_1^*$, $R_2^*$ and $R_3^*$ are as defined for a compound of the formula II above, L is a cleavable linker, RES is a solid resin, and n is a natural number not including 0; and removing the protecting group Prot***.

(viii/b) In a further embodiment, the invention relates to the method or process according to the preceding paragraph (vii/b), further comprising, for the synthesis of a compound of the formula XII, especially XIIA, coupling a resin bound dipeptide symbolized by the formula XIII,

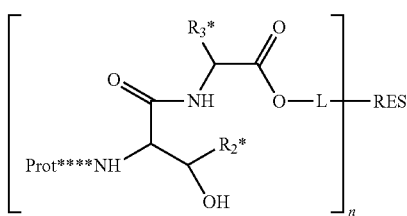

XIII especially XIIIA

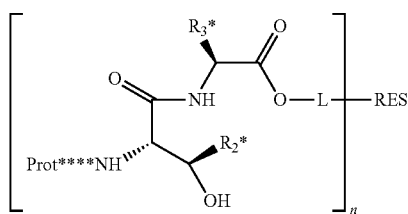

XIIIA in which Prot**** is a protecting group that can be cleaved off selectively without affecting other protecting groups present in a compound of the formula II as defined above and with the product remaining on the resin, $R_2^*$ and $R_3^*$ are as defined for a compound of the formula II above, L is a cleavable linker, RES is a solid resin, and n is a natural number not including 0, after removal of the protecting group Prot**** via the thus obtainable free amino group, with an amino acid of the formula XIV,

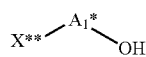

XIV in particular of the formula XIV*,

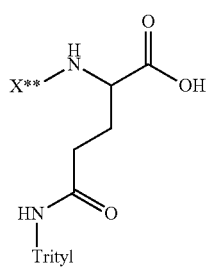

XIV* more particularly of the formula XIV**,

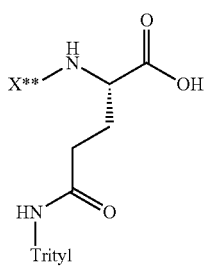

XIV** wherein X** is an amino protecting group or is X*, and wherein X* and $A_1^*$ are as defined for a compound of the formula II above, or a reactive derivative of said acid; and, if X is an amino protecting group, removing said amino protecting group X to yield the derivative of formula II wherein, instead of X*, H is present and coupling the resulting amino group with an acyl group X* using the corresponding acid X*—OH wherein X* is as defined for a compound of the formula II above, or a reactive derivative of said acid.

(ix/b) A yet further embodiment of the invention relates to the method or process according to the preceding paragraph (viii/b), further comprising, for the synthesis of a compound of the formula XIII, especially XIIIA, coupling a resin bound amino acid symbolized by the formula XV,

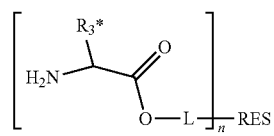

XV especially XVA,

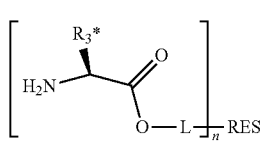

XVA wherein $R_3^*$ is as defined for a compound of the formula II above, L is a cleavable linker, RES is a solid resin, and n is a natural number not including 0, with an amino acid of the formula XVI,

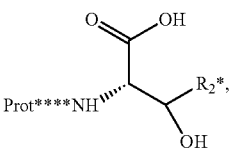

XVI especially XVIA,

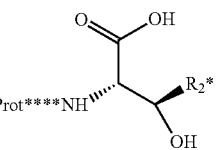

XVIA wherein Prot**** is a protecting group that can be cleaved off selectively without affecting other protecting groups present and with the product remaining on the resin, and $R_2^*$ is as defined for a compound of the formula II above, or a reactive derivative of said amino acid.

(x/b) A further embodiment of the invention relates to the method or process according to the preceding paragraph (ix/b), further comprising, for obtaining the resin bound amino acid of the formula XV, especially XVA, coupling an amino acid of the formula XVII,

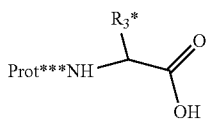

XVII especially XVIIA,

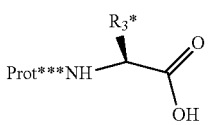

XVIIA wherein R₃* is as defined for a compound of the formula II above or below and Prot* is an amino protecting group can be cleaved off selectively without affecting other protecting groups present and with the product remaining on the resin; or a reactive derivative of said amino acid of the formula IX, to a cleavable linker L which is bound to a solid resin RES, and removing the protecting group Prot*.

(i/c) Another embodiment of the invention relates to the method or process according to any one of the preceding paragraphs (i/a) to (x/b) where the symbols $A_1, R_2, R_3, R_5, R_6, R_7$, X and Y or the corresponding unprotected or protected moieties $R_2^*, R_3^*, R_5^*, R_6^*, R_7^*, X^*$ and Y are selected so that, in the resulting compound of the formula I, or a salt thereof, $A_1$ is the bivalent radical of L-glutamine bound via the carbonyl of its α-carboxy group to the amino group at the right of $A_1$ in formula I and via its α-amino group to X, or is 2S-(2-hydroxy-3-phosphonooxy)-propionyl;

$R_2$ is methyl;

$R_3$ is isopropyl, isobutyl (2-methyl-n-propyl wherever used), especially isobutyl;

$R_5$ is sec-butyl or benzyl, especially sec-butyl;

$R_6$ is 4-hydroxybenzyl;

$R_7$ is isopropyl or sec-butyl (1-methyl-n-propyl wherever used), especially sec-butyl;

X is acetyl or isobutyryl, or is absent if $A_1$ is 2S-(2-hydroxy-3-phosphonooxy)-propionyl and Y is methyl.

(i/d) In another particular embodiment, the invention relates to a method or process for converting a dehydrate obtained from a compound of the formula II, especially IIa, of a compound of the formula I given obtained from a compound of the formula II above or in particular with the substituents as defined in the preceding paragraph (i/c) into the corresponding compound of the formula I, where the dehydrate has the formula XVIII,

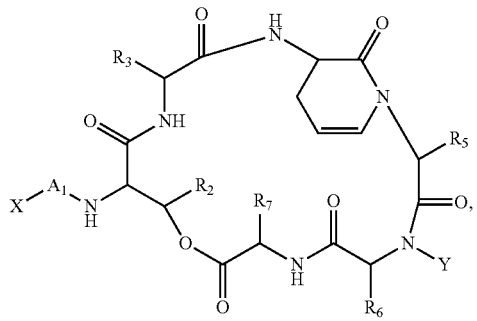

XVIII especially XVII IA,

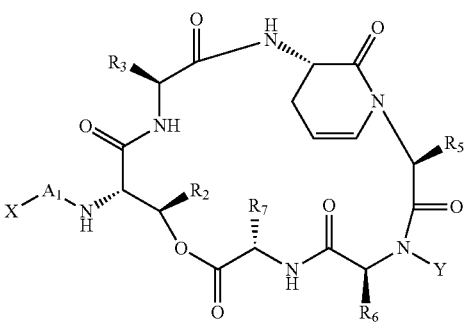

XVIIIA in which Y, X, $A_1$, $R_2$, $R_3$, $R_5$, $R_6$ and $R_7$ are as defined for a compound of the formula I above;

or especially a method or process for shifting the equilibrium of a mixture of a compound of the formula I and its corresponding dehydrate, and/or its corresponding hemiaminal analogue with a five-ring instead of the ahp structure in formula I which may also be formed as byproduct and has the formula XIX,

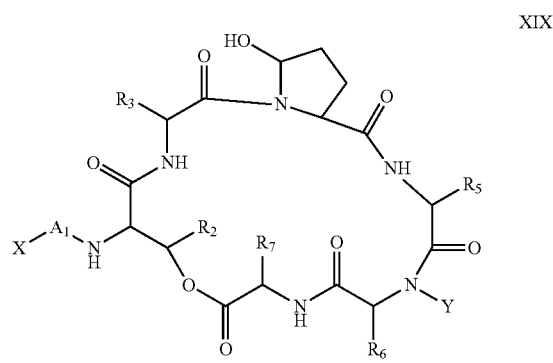

XIX especially the formula XIXA,

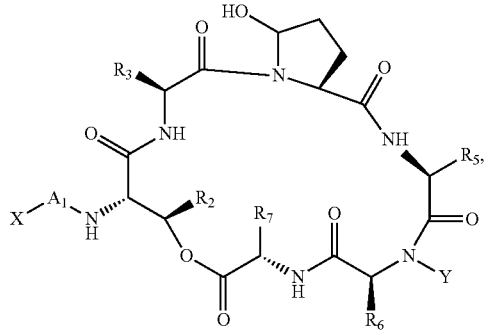

VIXA especially of the formula XXA,

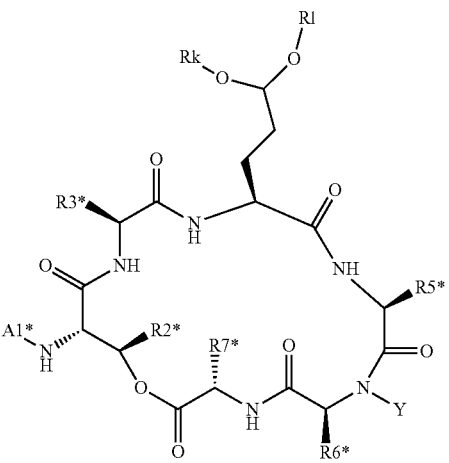

XXA in which Y, X, $A_1$, $R_2$, $R_3$, $R_5$, $R_6$ and $R_7$ are as defined for a compound of the formula I above, respectively;
in favor of the compound of the formula I,
said method or process comprising using an aqueous acid as reactive solvent to drive the reaction. This method is especially used in addition to the other processes or methods described above and below to increase the yield or to reconvert a compound of the formula V, especially VA, and/or the analogue with a five-membered ring instead of the ahp structure in formula I, into the corresponding compound of the formula I.

The method described for the conversion of the dehydrate and/or the five ring analogue (always regarding the desired ahp ring) into the desired compound of the formula I or especially IA, e.g. of Compound A-dehydrate from Example 3B into Compound A, enables a straight-forward synthesis of this class of compounds. Up to now, an acidic treatment as final step had to be circumvented in order to avoid the dehydration of the product.

(i/e) A further embodiment of the invention relates to the method according to the preceding paragraph (i/d), wherein the acid is a carboxylic acid, especially a halo substituted $C_{1-8}$alkanoic acid, more especially trifluoroacetic acid or trichloroacetic acid.

(i/f) The invention, in yet a further embodiment, relates to a compound of the formula XX,

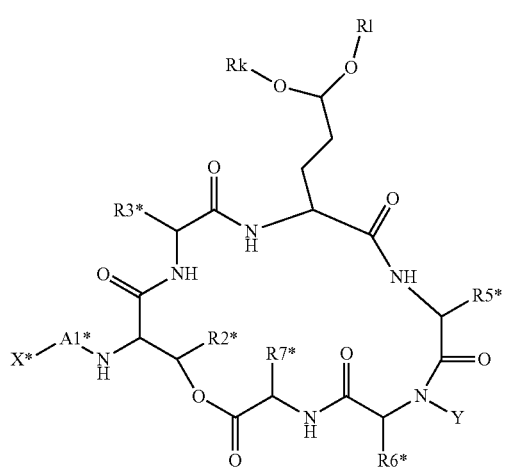

XX wherein Rk and Rl are as defined for a compound of the formula II above, Y is as defined for a compound of the formula I in the first instance above or in particular as defined above under (i/c) and $X^*$, $A_1^*$, $R_2^*$, $R_3^*$, $R_5^*$, $R_6^*$, and $R_7^*$ correspond to X, $A_1$, $R_2$, $R_3$, $R_5$, $R_6$, and $R_7$ in formula I as defined above or below or in paragraph (ia) or especially under (i/c) given above, respectively, however with the proviso that reactive functional groups on these moieties are preferably present in protected form.

(i/g) In a further embodiment, the invention relates to a novel compound selected from the group consisting of compounds of the formula II, III, III*, IV and V, and especially of the formula IIA, IIIA, IIIA*, IV and VA yet more especially to the group consisting of the following (especially enantiomerically enriched or pure) compounds: Compound 2*, Compound 3*, compound 5*, preferably Compound 2A*, Compound 3A*, Compound 4A*, Compound 5A*, especially in the form given in the examples: Compound 2, Compound 3, Compound 5, Compound 6, Compound 7, Compound 8, Compound A, Compound 9 and Compound 10 and enantiomerically enriched or especially pure Compound 4, as well as compounds 12, 14, 15, 16 and 17. Also preferred are the compounds of the formulae 12*, 12A*, 14*, 14A*, 15*, 15A*, 16*, 16A*, 17* or 17A* given below, in which Rl and Rk independently of each other are 1-aralkyl, such as 1-($C_6$-$C_{12}$aryl)-$C_1$-$C_7$alkyl, more especially benzyl, as well as the corresponding compounds wherein Rl and Rk together form an unsubstituted or substituted alkylene, especially —$CH_2$—$CH_2$— or —$CH_2$—$CH_2$—$CH_2$—.

(i/h) In yet a further embodiment, the invention relates to a method or a process for the synthesis of a compound of the formula V, especially of the formula VA mentioned above, according to either (a) (especially) in the case of the synthesis of a compound of the formula V wherein Rk and Rl together form an unsubstituted or substituted lower alkylene bridge, especially —$CH_2$—$CH_2$— or —$CH_2$—$CH_2$—$CH_2$—, the following reaction scheme, alternatively via the route (i) 1*→2*→3*, (ii) 1*→2*→4*→5*, or (iii) 1*→2*→3*→5*:

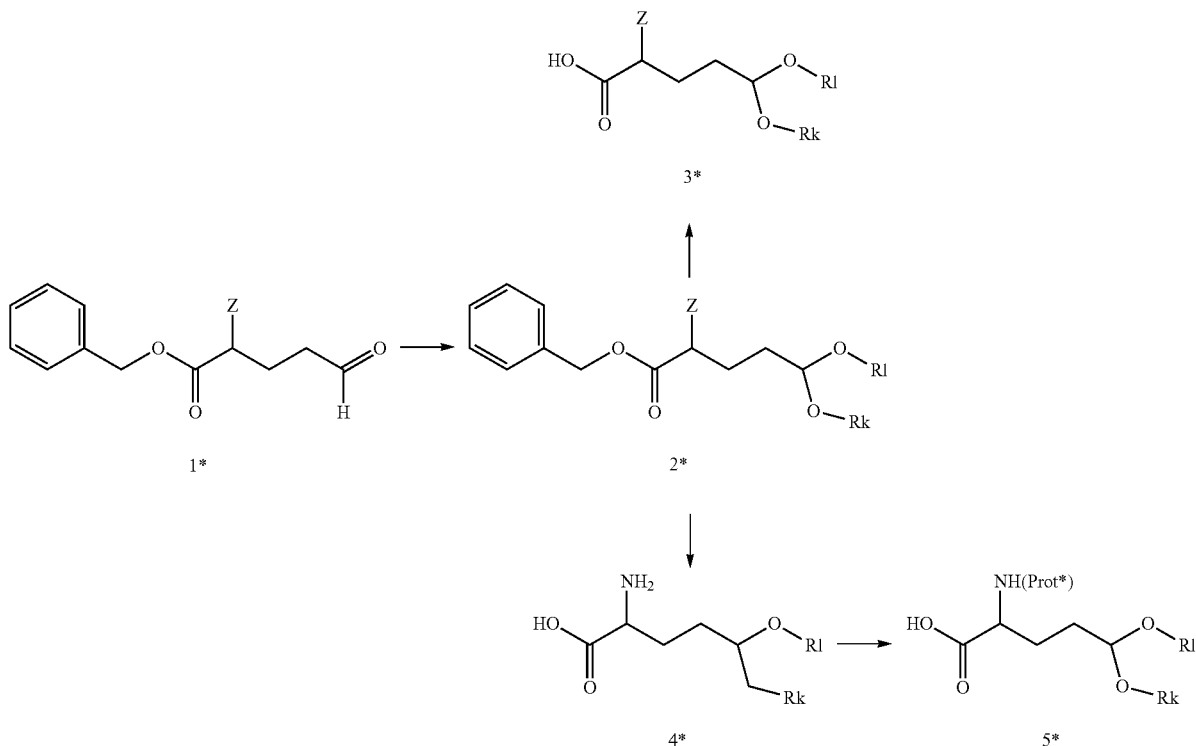

(wherein Rk, Rl have the meanings just indicated and Z has the meanings mentioned above for a compound of the formula V, especially in the compounds 1*, 2* and 3* being N(Prot**)₂ as defined for a compound of the formula V, especially 1-(C₆-C₁₂-aryl)-C₁-C₆-alkyl, especially benzyl, and in the compound 5* being NHProt* as defined for a compound of the formula V, Prot* especially being an acyl protecting group, e.g. fluoren-9-yl-methoxycabonyl, and the compounds of formula 3* and 5* each correspond to a compound of the formula V;

or especially, to obtain a compound of the formula VA, the following scheme, alternatively via the route (i) 1A*→2A*→3A*, (ii) 1A*→2A*→4A*→5A*, or (iii) 1A*→2A*→3A*→5A*:

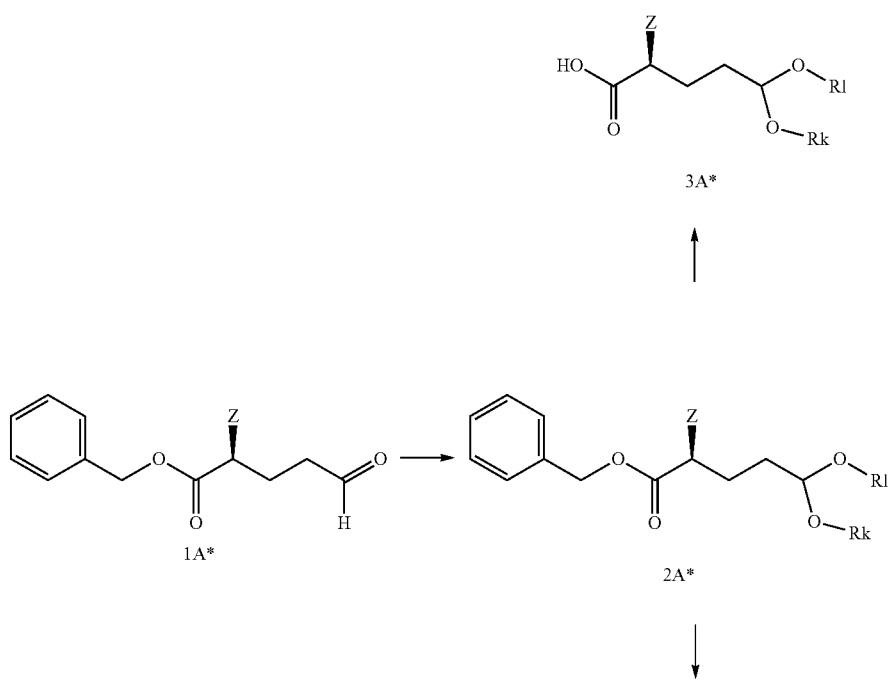

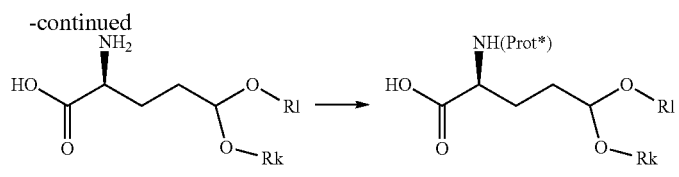

4A*  →  5A*

(wherein Rk, Rl have the meanings just indicated and Z and Prot* have the meanings mentioned above for a compound of the formula V, especially Z in the compounds 1A*, 2A* and 3A* being 1-($C_6$-$C_{12}$-aryl)-$C_1$-$C_6$-alkylamino, especially benzylamino, and Prot* in the compound 5A* being an acyl protecting group, e.g. fluoren-9-yl-methoxycabonyl, where the compounds of formula 3A* and 5A* each correspond to a compound of the formula VA;

where the reaction of 1* or 1A* to 2* or 2A* is an acetal formation reaction with an unsubstituted or substituted lower alkylendiol, especially ethylene glycol, e.g. in an appropriate solvent, such as dichloromethane, in the presence of an acid, such as toluene sulfonic acid, in the presence of e.g. molecular sieve; the reaction of 2* or 2A* to 3A or 3A* by hydrolysis in the presence of a base, such as an alkali metal hydroxide, e.g. LiOH, in an ether, e.g. dioxane, and water; or the alternative reaction from 2*, especially 2A* to 4*, especially 4A*, under deprotection of the carboxy and the amino group is made by e.g. catalytic hydrogenation, e.g. hydrogenation with a noble metal catalyst, e.g. Pd or Pt, e.g. on a carrier such as aluminium oxide or carbon, an appropriate solvent, e.g. an alcohol, such as methanol, ethanol or isopropanol, followed by reintroduction of an amino protecting group Prot**, especially an acyl protecting group, such as fluoren-9-yl-methoxycarbonyl, e.g. under acylation conditions or in the presence of a coupling agent as mentioned below for amino acid or acid couplings to amino groups, especially using the (e.g.Fmoc-) HOSU-ester, a tertiary base, e.g. triethylamine, and an appropriate solvent, e.g. water and/or acetonitrile; where alternatively the compound of formula 4*, especially 4A*, may be obtained from a compound of the formula 3*, especially 3A*, by catalytic hydrogenation as just mentioned;

and where the compound 1* or 1A* may be obtained by or in analogy to the method mentioned in Rodriguez and Taddei, Synthesis 2005, 3, pp. 493-495);

or (b) (especially in the case of the synthesis of a compound of the formula V, especially VA mentioned above, wherein each of Rk and Rl is an unsubstituted or substituted alkyl moiety, especially 1-aralkyl, such as 1-($C_6$-$C_{12}$aryl)-$C_1$-$C_7$alkyl, more especially benzyl) according to the following reaction scheme:

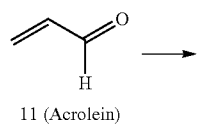

11 (Acrolein)

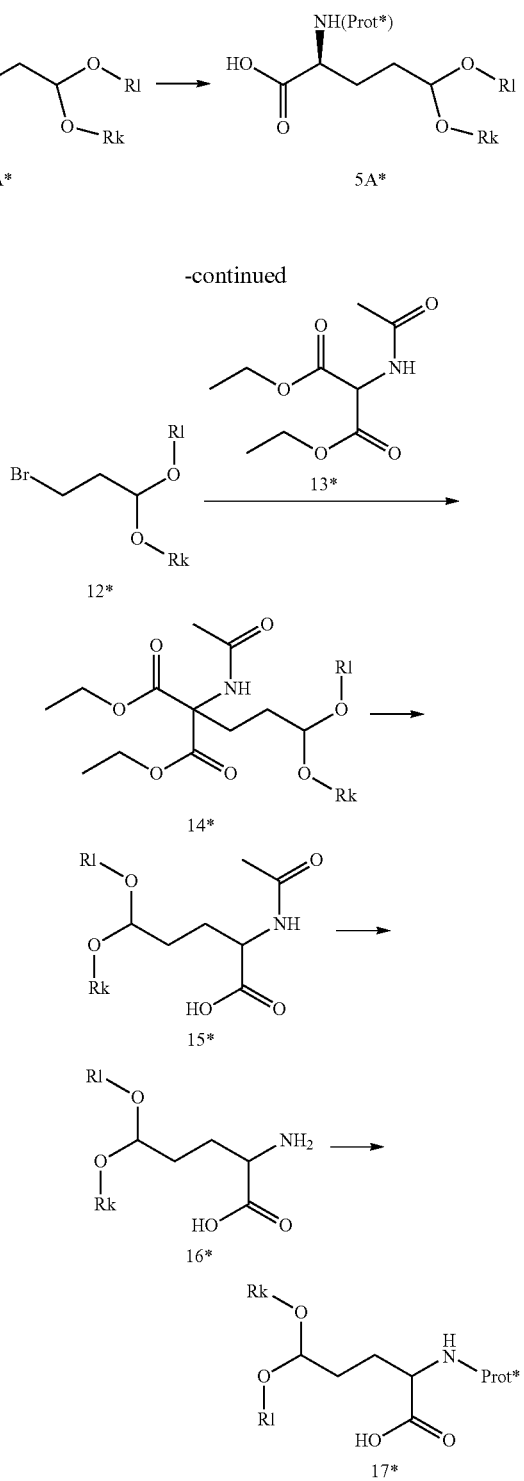

(wherein Rk, Rl have the meanings just indicated and Prot* has the meanings mentioned above for a compound of the formula V, especially in the compounds 17* being an acyl protecting group, e.g. fluoren-9-yl-methoxycabonyl, and the compounds of formula 17* correspond to a compound of the formula V;

or especially, to obtain a compound of the formula VA, the following scheme:

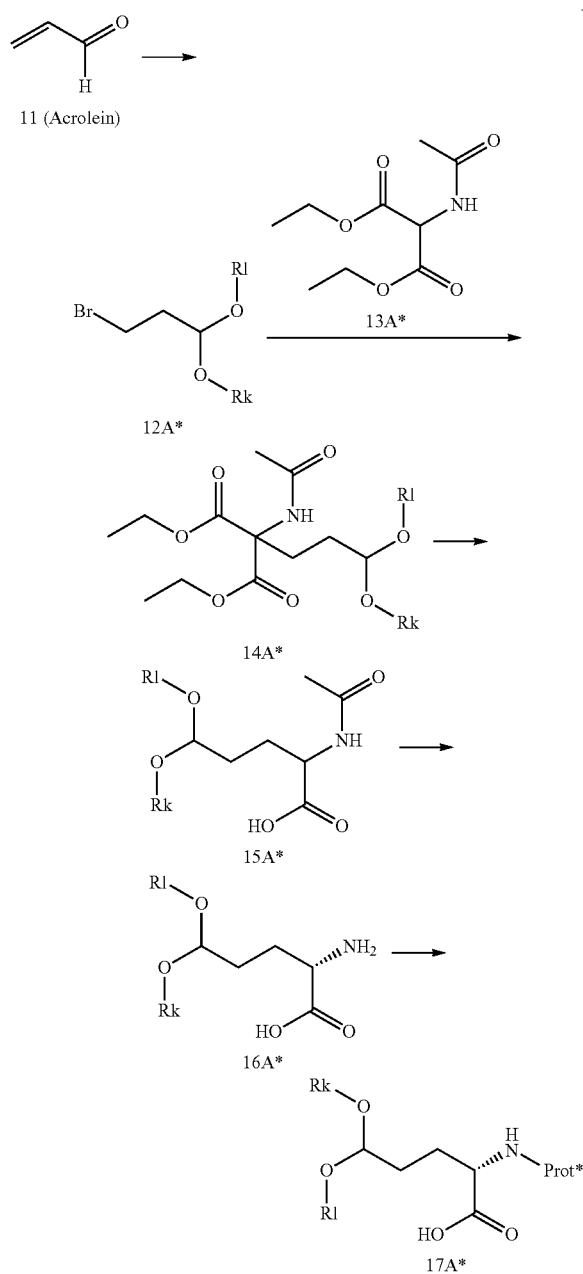

(wherein Rk, Rl have the meanings just indicated and Prot* has the meanings mentioned above for a compound of the formula V, especially in the compounds 17A* being an acyl protecting group, e.g. fluoren-9-yl-methoxycabonyl, and the compounds of formula 17A* correspond to a compound of the formula VA;
where preferably the reaction of 11 with 12 or 12A* takes place in an appropriate solvent, e.g. methylene chloride, with a brominating agent, e.g. trimethylbromosilane, followed by the addition of compounds of the formula Rk-OH and Rl-OH (which are preferably identical) and a mixture or tertiary base, e.g. pyridine and N,N-dimethylaminopyridine, and an acid anhydride, e.g. acetic anhydride; reaction of the compound 12* or 12A* with a compound of the formula 13* or 13A* in an appropriate solvent, e.g. an acid amide, such as dimethylformamide, a strong base, e.g. potassium tert-butoxide; hydrolysis of the resulting compound of the formula 14*, especially 14A*, with an alkali metal hydroxide, e.g. potassium hydroxide, in an appropriate solvent, e.g. an alcohol, such as ethanol, and subsequent warming up for decarboxylation to give a compound of the formula 15*, especially 15A*, removal of the acetyl group in an appropriate buffer, e.g. in the range of pH 7 to 10, e.g. in aqueous citrate buffer titrated with an alkali metal hydroxide, such as sodium hydroxide, with an acylase, if required in the presence of cofactors such as cobalt chloride, to give a compound of the formula 16*, especially 16A*; and introduction of a protecting group Prot**, e.g. acyl, e.g. 9-fluorenylmethoxycarbonyl, with an appropriate reagent, e.g. Fmoc-OSU, in an appropriate solvent, e.g. water and/or acetonitrile.

The following definitions (or also definitions already included above) can replace more general terms used in invention embodiments above and below in order to define further embodiments of the invention, with either one, two or more or all general terms being replaceable by the more specific terms in order to define such invention embodiments:

In all reactions, protecting gas may be used, such as nitrogen or Argon, where appropriate or necessary, and the temperatures are as known to the person skilled in the art, e.g. in the range from −25° C. to the reflux temperature of the respective reaction mixture, e.g. from −20 to plus 90° C.

If Rk and Rl are each independently of each other unsubstituted or substituted alkyl, this refers especially to $C_1$-$C_7$-alkyl or especially 1-aralkyl, such as 1-($C_6$-$C_{12}$aryl)-$C_1$-$C_7$alkyl, more especially benzyl.

If Rk and Rl together with the two binding O atoms and the carbon atom to which the two O atoms are bound form a ring that is unsubstituted or substituted, Rk and Rl then preferably form an unsubstituted or substituted alkylene bridge, especially unsubstituted or substituted ethylen, such as —$CH_2$—$CH_2$—), where the substituent(s) may preferably be selected from $C_1$-$C_7$-alkyl, especially two such substituents, such as methyl, ethyl, n-propyl or isopropyl.

A bivalent moiety of an amino acid with a terminal carboxy or carbamoyl group is preferably an alpha-carbamoyl or carboxyl-$C_{1-8}$-substituted amino acid, especially the bivalent moiety of asparagine or glutamine, and is bound at its right hand side in formula I via a carbonyl (preferably the carbonyl of its α-carboxyl group) to the rest of the molecule.

$C_{1-8}$-alkanoyl or phosphorylated hydroxy-$C_{1-8}$-alkanoyl ($C_{1-8}$-alkanoyl carrying both a hydroxyl and a phosphono (—O—P(=O)(OH)$_2$) group) $A_1$ is e.g. 2,3-dihydroxy-propanoyl (preferably in S-form) or 2-hydroxy-3-phosphonopropanoyl (preferably in S-form).

$R_2$ and $R_2$* are $C_{1-8}$-alkyl, especially methyl wherever mentioned.

$R_3$ is the side chain of an amino acid, especially of a natural amino acid. Preferably, it is $C_{1-8}$alkyl which may be branched or linear. Most especially, $C_{1-8}$alkyl is n-(2-methyl)propyl (isobutyl), n-(1-methylpropyl (sec-butyl) or methyl, that is, the amino acid carrying the moiety is leucine, isoleucine or valine.

$R_3$* is the corresponding side chain in protected form if a functional group is present that has to be hindered to participate in a reaction. Preferably, it is $C_{1-8}$alkyl which may be branched or linear, especially as defined in the preceding paragraph.

A "side chain of an amino acid" may be selected from any moiety, e.g. a mono- or polycyclic, linear, saturated, unsaturated (e.g. with conjugated double bonds) or partially saturated organic moiety, e.g. with up to 20 carbon atoms and 0 to 5 heteroatoms in the basis structure independently selected from N, O and S replacing the corresponding number of carbon atoms, and may be substituted by up to three moieties selected from amino, imino, hydroxy, carboxy, carbamoyl, sulfhydryl, amidino, guanidino, O-phosphono(—O—P(=O)(OH)$_2$). Preferably, the side chains are selected from those of the 20 standard alpha-amino acids arginine, histidine, lysine, aspartic acid, glutamic acid, serine, threonine, asparagine, glutamine, cysteine, glycine, alanine, leucine, isoleucine, methionine, phenylalanine, tryptophan, tyrosine, valine and further proline (then with internal cyclization including the alpha-amino group).

For the amino acids, either their names or the customary three letter codes are used in the present disclosure, in accordance with the following table:

| Amino acid | Three letter code |
| --- | --- |
| Alanine | Ala |
| Arginine | Arg |
| Asparagine | Asn |
| Aspartic acid | Asp |
| Asparagine or aspartic acid | Asx |
| Cysteine | Cys |
| Glutamic acid | Glu |
| Glutamine | Gln |
| Glutamine or glutamic acid | Glx |
| Glycine | Gly |
| Histidine | His |
| isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Try |
| Tyrosine | Tyr |
| Valine | Val |

$R_5$ is the side chain of an amino acid, preferably a standard amino acid. Preferably, it is $C_{1-8}$alkyl which may be branched or linear and which is unsubstituted or substituted by phenyl. Most especially it is benzyl, n-(2-methyl)propyl, isobutyl or methyl, that is, the amino acid carrying the moiety is phenylalanine, leucine, isoleucine or valine.

$R_6$ is the side chain of a hydroxy amino acid, especially of tyrosine.

$R_7$ is the side chain of an amino acid, especially of a natural amino acid. Preferably, it is $C_{1-8}$alkyl which may be branched or linear. Most especially it is n-(2-methyl)propyl(isobutyl), n-(1-methyl)propyl (sec-butyl) or methyl, that is, the amino acid carrying the moiety is leucine, isoleucine or valine.

$C_{1-8}$-alkyl can be linear or branched one or more times; for example, it can be n-(2-methyl)propyl, n-(1-methyl)propyl or methyl.

All of the compounds can, where salt-forming groups such as basic groups, e.g. amino or imino, or acidic groups, e.g. carboxyl or phenolic hydroxyl, are present, be used in free form or as salts or as mixtures of salts and free forms. Thus where ever a compound is mentioned, this includes all these variants. For example, basic groups may form salts with acids, such as hydrohalic acids, e.g. HCl, sulfuric acid or organic acids, such as acetic acid or trifluoroacetic acid, while acidic groups may form salts with positive ions, e.g. ammonium, alkylammonium, triethylamine, N-methylmorpholine, dimethylaminopyridine, alkali or alkaline-earth metal salt cations, e.g. Ca, Mg, Na, K or Li cations, or the like, or zwitterionic salts or inner salts of the compounds may be present.

"Or the like" or "and the like", wherever used in this disclosure, refers to the fact that other alternatives to those mentioned preceding such expression are known to the person skilled in the art and may be added to those expressions specifically mentioned; in other embodiments, "or the like" and "and the like" may be deleted in one or more or all invention embodiments.

Acetal protecting groups are highly sensitive to acidic conditions, especially in the presence of water. Cleavage of the acetal protecting group during the solid phase peptide synthesis or during cleavage from solid support would generate the free aldehyde function, which could react with the free amino group and undergo other side reactions. Therefore, it is important to keep the acetal protecting group until the cyclization of the oligopeptide is performed to obtain the macrocyclic compound II or IIA.

The protecting groups Prot, Prot*, Prot**** and any further protecting groups present on the moieties A*, $R_2$*, $R_3$*, $R_5$*, $R_6$*, $R_7$*, X*, where ever mentioned throughout the present description and claims, are selected so that they allow for orthogonal protection.

Orthogonal protection is a strategy allowing the deprotection of multiple protective groups one (or more but not all) at the time where desired each with a dedicated set of reaction conditions without affecting the other protecting group(s) or bonds to resins, e.g. via linkers on solid synthesis resins. In other terms: The strategy uses different classes of protecting groups that are removed by different chemical mechanisms, also using appropriate linkers in the case of solid phase peptide synthesis (where the linker-resin bond might together be considered as a carboxy protecting group).

Preferably, the protecting groups are selected as follows:

Prot* (a protecting group that can be removed (=is appropriate for removal) during the cleavage of IV, especially IVA, during the reaction under (iii/b) or subsequently but, on the other hand, can be removed on the resin without cleaving other bonds (no cleavage of an amino acid or peptide bound via the carbonyl of its (especially α-carboxyl group to the binding via a linker L mentioned below; also without cleaving off other protecting groups present), especially a protecting group removable without cleavage of an ester (instead of an amide) bond in a depsipeptide or depsipeptide precursor and under conditions other than those for other protecting groups present, while preserving the binding via the linker to a resin RES where present; it is preferably removable by a mild base, e.g. piperidine, morpholine, dicyclohexylamine, p-dimethylamino-pyridine, diisopropylamine, piperazine, tris-(2-aminoethyl)amine in an appropriate solvent, e.g. N,N-dimethylformamide, methylene chloride; Prot** is, e.g., selected from the group consisting of fluoren-9-ylmethoxycarbonyl (Fmoc); 2-(2' or 4'-pyridyl)ethoxycarbonyl and 2,2-bis(4' nitro-phenyl)ethoxycarbonyl.

Prot** is a protecting group that can be removed (especially from a compound of the formula III* or especially IIIA*) under conditions that are different to those of the cleaving reaction under (iii/b) especially arylalkyl, especially 1-($C_6$-$C_{12}$aryl)-$C_1$-$C_4$alkyl, more especially benzyl, which can be removed e.g. by catalytic hydrogenation, e.g. with hydrogen in the presence of a noble metal catalyst, such as Pd or Pt which may be on a carrier, such as aluminium oxide or especially carbon.

Prot*** (an amino protecting group that can be cleaved off selectively without affecting other protecting groups present and with the product remaining on the resin) is selected from those mentioned for Prot*, e.g. fluoren-9-ylmethoxycarbonyl (Fmoc), each of which can be removed e.g. as mentioned above or below.

Prot** is a protecting group that can be cleaved off selectively without affecting other protecting groups present, especially as defined for Prot*.

The preferred orthogonal synthesis method in this case makes use of the Fmoc-protecting group strategy known in general for peptide synthesis using solid phase and liquid phase peptide synthesis.

The aldehyde protecting group(s) Rk and Rl (which together with the binding O atoms and the carbon binding them form a protected aldehyde group (an acetal) can be removed in the presence of water by acid catalysis, especially an alpha-halo substituted alkanoic acid, such as trifluoroacetic acid or trichloroacetic acid.

Other protecting groups present as well as the binding linker to a resin RES where present are preferably not removable under conditions under which Prot*, Prot, Prot* and Prot**** can be removed, e.g. in A*, carbamoyl can be N-protected e.g. with trityl (triphenylmethyl) (cleavage e.g. with trifluoro acetic acid (TFA); (e.g. in $R_6$*) a tyrosine hydroxy can be Boc (tert-butoxycarbonyl) protected, or protected by tert-butyldimethyl-silyl, methoxymethyl or arylacetate (cleavage e.g. with TFA) and more preferably under conditions under which the bond to the linker to the Resin RES is preferably not cleaved or (where simultaneous deprotection and cleavage from the resin to the bond is desired) also cleaved (e.g. cleavage with acid, such as TFA).

Appropriate protecting groups are known in the art, as well methods for their introduction and removal. For example, the protecting groups, their introduction and removal methods may be selected from those described in standard textbooks such as "Protective Groups in Organic Synthesis", $3^{rd}$ ed., T. W. Green and P. G. M. Wuts (Eds.). J. Wiley & Sons, Inc., New York etc. 1999.

The protecting groups Prot*, Prot, Prot*, Prot**** and other protecting groups are thus not limited to those mentioned above—rather they should fulfill conditions that make them appropriate for orthogonal protection, e.g. as described above or below.

It is recommended to avoid too basic conditions (though the bases described for Fmoc cleavage, such as piperidine, are usually allowable) to avoid cleavage of the depsipeptide (ester) bond.

An appropriate solvent or solvent mixture useful during the deprotection steps may, e.g., be selected from customary solvents, e.g. an N,N dialkylformamide, such as dimethylformamide, a halogenated hydrocarbon, e.g. dichloromethane, alkanols, such as ethanol, propanol or isopropanol, nitriles, e.g. acetonitrile, alkanoic acid amides, such as dimethylformamide or diethylformamide, or further an aromatic hydrocarbon, e.g. toluene, or mixtures of two or more, also water may be present. The temperatures may be ambient temperature or lower or higher, e.g. in the range from −20° C. to 50° C.

Among the possible solid support for Solid Phase Peptide Synthesis (SPPS), the following may be mentioned:

Gel-type supports without or with spacer: These are highly solvated polymers with an equal distribution of functional groups. This type of support is the most common, and includes:

Polystyrene: Styrene cross-linked with e.g. 1-2% divinylbenzene; Polyacrylamide or polymethacrylamide: as hydrophilic alternative to polystyrene; Polyethylene glycol (PEG): PEG-Polystyrene (PEG-PS) is more stable than polystyrene and spaces the site of synthesis from the polymer backbone; PEG-based supports: Composed of a PEG-polypropylene glycol network or PEG with polyamide or polystyrene (these already include a spacer, PEG);

Surface-type supports: Materials developed for surface functionalization, including controlled pore glass, cellulose fibers, and highly cross-linked polystyrene.

Composites: Gel-type polymers supported by rigid matrices.

Usually these gels carry reactive groups to which a linker L as mentioned for various precursors above and below can be bound. For example, such groups include aminomethyl groups, polyethyleneglycol groups with a terminal hydroxy, and the like.

Any such support can be used in the embodiments of the present invention.

Gel type supports are used in another special embodiment of the invention, Among these, polystyrene (divinylbenzene crosslinked); polyacrylamide and polymethacrylamide resins are especially preferred.

Among the possible linkers, all commonly known and appropriate may be used.

Examples in possible embodiments of the invention are the 2-methoxy-4-benzyloxy-benzyl alcohol linker (a Sasrin-Linker, Sasrin stands for superacid sensitive resin, binds the amino acids or peptides via alcoholic OH); the trityl linker family (e.g., Trityl, 2Cl-Trityl, which bind the amino acids or peptides via OH); the 4-(2,4-dimethoxyphenylhydroxy-methyl)phenoxymethyl-Linker (Rink-Acid-Linker, binds the amino acids or peptides via OH); or tris(alkoxy)benzyl ester linkers (HAL-Linker, binds the amino acids or peptides via OH).

The introduction of linker groups and their coupling with amino acids can be conducted essentially as described or in analogy to the Examples. For example, in the case of trityl ester formation, the resin (e.g. divinylbenzene cross-linked aminomethylpolystyrene resin) may be suspended in an appropriate solvent, such as a dialkyl acid amide, e.g. dimethylformamide, and/or an alcohol, such as ethanol, propanol or isopropanol, and reacted with a hydroxyaryl-acid linker, e.g. 4-(diphenylhydroxymethyl)-benzoic acid, in the presence of a coupling agent, e.g. mentioned below for the coupling of acids, e.g. 1-hydroxybenzotrialzoe and dicyclohexycicarbodiimide; or, for the manufacture on chloro-(2' chloro) triytl-polystyrene resin, the resin is suspended in an appropriate solvent, e.g. dichloromethane, addition of a chlorinating agent, e.g. acetyl chloride, and then reaction with the carboxyl group of an amino acid (this term always including unprotected or protected amino acids), e.g. in the presence of a base, e.g. a tertiary amino base, such as N-methyl-morpholine.

The cleavage of completed (protected or unprotected) peptides, e.g. to achieve the linear precursor peptide of formula III, especially IIIA, or III*, especially III*A, can then be conducted under mild acidic conditions, e.g. in the presence of an organic alkanoic acid, such as acetic acid, in an appropriate solvent, e.g. in dichloromethane or trifluoroethanol.

The cleavage conditions from the solid support must be selected such that the other protecting groups present in the molecule such as the trityl-, t-butyl- and in particular the acetal-protecting groups are not cleaved. Acetal protecting groups are highly sensitive to acidic conditions, especially in the presence of water. Cleavage of the acetal protecting group during the solid phase peptide synthesis or during cleavage from solid support would generate the free aldehyde function, which could react with the free amino group and undergo other side reactions.

Where reactive derivatives of acids, especially amino acids, or peptides, e.g. dipeptides, are mentioned, they may be formed in situ or may be used as such.

Reactive (or active) derivatives used as such include the halogenides, e.g. chlorides, or nitrophenyl esters, e.g. the 2,4-dinitrophenyl esters, or acid anhydrides (symmetric or e.g. with acetic acid) of the carboxy groups of the acids to be reacted.

For in situ formation, customary coupling agents may be applied. Such reagents are known to the person skilled in the art and can be deduced conveniently from many sources, e.g. Aldrich ChemFiles—Peptide Synthesis (Aldrich Chemical Co., Inc., Sigma-Aldrich Corporation, Milwaukee, Wis., USA) Vol. 7 No. 2, 2007 (see hftp://www.sigmaaldrich.com/etc/medialib/docs/Aldrich/Brochure/al_chemfile_v7_n2. Par. 0001.File.tmp/al_chemfile_v7_n2.pdf). Among the possible coupling agents for amide and ester bond synthesis the following may be mentioned:

Triazoles, uronium or hexafluorophosphonium derivatives, e.g. 1-hydroxy-benzotriazole (HOBt), 1-hydroxy-7-aza-benzotriazole (HOAt), ethyl 2-cyano-2-(hydroxyimino) acetate, 2-(1H-7-Azabenzotriazol-1-yl)-1,1,3,3-tetramethyluronium hexafluorophosphate methanaminium (HATU), benzotriazol-1-yl-oxytripyrrolidinophosphonium hexafluorophosphate (PyBOP), 1-(mesitylene-2-sulfonyl)-3-nitro-1,2,4-triazole (MSNT), 2-(1H-benzotriazol-1-yl)-1,1,3,3-tetramethyluronium-hexafluorophosphate (H BTU), 2-(1H-benzotriazol-1-yl)-1,1,3,3-tetramethyluronium-hexafluoroborate (T BTU), 2-succinimido-1,1,3,3-tetramethyluronium-tetrafluoroborate (TSTU), 2-(5-norbornen-2,3-dicarboximido)-1,1,3,3-tetramethyl-uronium-tetrafluoroborate (TNTU), O-[(cyano(ethoxycarbonyl) methyliden)amino]-1,1,3,3-tetramethyluronium-tetrafluoroborate (TOTU), O-(benzotriazol-1-yl)-1,3-dimethyl-1,3-dimethylene uronium hexafluorophosphate (HBMDU), O-(benzotriazol-1-yl)-1,1,3,3-bis(tetramethylene)uronium hexafluorophosphate (HBPyU), O-(benzotriazol-1-yl)-1,1,3,3-bis(pentamethylene)uronium hexafluorophosphate (HBPipU), 3-hydroxy-4-oxo-3,4-dihydro-1,2,3-benzotriazine (HODhbt), 1-hydroxy-7-azabenzotriazole and its corresponding uronium or phosphonium salts, designated HAPyU and AOP, 1-cyano-2-ethoxy-2-oxoethylideneaminooxy-dimethylamino-morpholino-carbenium hexafluorophosphate (COMU), chlorotripyrrolidinophosphonium hexafluorophosphate (PyCloP), or the like;

Carbodiimides, e.g. dicyclohexylcarbodiimide, N-(3-dimethylaminopropyl)-N'-ethylcarbodiimide, 1-tert-butyl-3-ethylcarbodiimide, N-cyclohexyl-N'-2-morpholinoethyl)carbodiimide or diisopropylcarbodiimide (especially for ester formation via O-acyl urea formation of the carboxylic group); or active ester forming agents, e.g. 2-mercaptobenzothiazole (2-MBT), azide forming agents, e.g. diphenyl phosphoryl azide, acid anhydrides, such as propane phosphonic acid anhydride, acid halogenation agents, e.g. 1-chloro-N,N,2-trimethyl-1-propenylamine, chloro-N,N,N',N'-bis(tetramethylene)formamidinium tetrafluoroborate or hexafluorophosphate, chloro-N,N,N',N'-tetramethlformamidinium hexafluorophosphate, fluoro-N,N,N',N'-tetramethylformamidinium hexafluorophosphate, fluoro-N,N,N',N'-bis(tetramethylene) formamidinium hexafluorophosphate, or the like, or mixtures of two or more such agents.

Also for the ester coupling of compounds of the formula XI or XIA with those of the formula XII or XIIA, respectively, the corresponding reactive carboxyl compounds can be used or formed in situ. Here, especially MSNT is preferred as coupling agent as this allows for the maintenance of high stereospecificity.

For the macrolactonization of a compound of the formula III, especially IIIA, also coupling reagents and conditions as described for the coupling of amino acids can be used.

The reactions may, in each case, where appropriate, be conducted in the presence of a mild base (e.g. N-methylmorpholine, a trialkylamine, e.g. ethyldiisopropylamine, a di-(alkyl)aminopyridine, such as N,N-dimethylaminopyridine, or the like (taking care that the conditions are not so basic as to allow for the hydrolysis of ester groups, e.g. the depsipeptide ester group, present in precursors of the compound of the formula I), where appropriate or required in the presence of an appropriate solvent or solvent mixture, e.g. an N,N dialylformamide, such as dimethylformamide, a halogenated hydrocarbon, e.g. dichloromethane, N-alkylpyrrolidones, such as N-methylpyrrolidone, nitriles, e.g. acetonitrile, ethers, such as dioxane or tetrahydrofurane, or further an aromatic hydrocarbon, e.g. toluene, or mixtures of two or more, where, provided an excess of coupling agent is present, also water may be present. The temperatures may be ambient temperature or lower or higher, e.g. in the range from −20° C. to 50° C.

The amino acids of the formula VII, VIIA, IX, IXA, XI, XIA, XV, XVA, XVI, XVIA, XVII, XVII (obtainable e.g. by Solution Phase peptide synthesis) are known or they can be synthesized according to methods known in the art, they are commercially available, and/or they can be synthesized in analogy to methods known in the art.

Also the remaining starting materials, e.g. the acid of the formula XIV, are known or they can be synthesized according to methods known in the art, they are commercially available, and/or they can be synthesized in analogy to methods known in the art.

Coupling reactions for dipeptides make us of the corresponding carboxylic groups of amino acids in free form or in activated form.

EXAMPLES

The following examples illustrate the invention without limiting its scope.

ABBREVIATIONS aq. aqueous
Boc/BOC tert-Butoxycarbonyl
brine sodium chloride solution in water (saturated at RT)
Bzl benzyl
COMU 1-cyano-2-ethoxy-2-oxoethylideneaminooxy-dimethylamino-morpholino-carbenium hexafluorophosphate
DCM dichloromethane
DIPEA N,N-diisopropylethylamine
DMAP 4-Dimethylaminopyridine
DMF N,N-dimethylformamide
Fmoc/FMOC 9-fluorenymethoxycarbonyl
Fmoc-OSu N-(9-Fluorenylmethoxycarbonyloxy)succinimide
Et ethyl
h hour(s)
HATU 2-(1H-7-Azabenzotriazol-1-yl)-1,1,3,3-tetramethyluronium hexafluorophosphate Methanaminium
HOSU N-Hydroxysuccinimide
HPLC High Performance Liquid Chromatography
HR-MS High Resolution Mass Spectroscopy IPC In-Process Control
IR Infrared Spectroscopy
IT internal temperature
Kaiser test Ninhydrin-based test to monitor deprotection in SPPS (see E. Kaiser, R. L. Colescott, C. D. Bossinger, P. I. Cook, Analytical Biochemistry 34 595 (1970)); if mentioned to be OK, this means successful deprotection.
Me methyl
MED Dichloromethane
MS Mass Spectroscopy
MSNT 1-(Mesitylene-2-sulfonyl)-3-nitro-1,2,4-triazole
NMR Nuclear Magnetic Resonance Spectroscopy
PyBOP benzotriazol-1-yl-oxytripyrrolidinophosphonium hexafluorophosphate
RP Reversed Phase
RT/rt room temperature
SPPS Solid Phase Peptide Synthesis
TBME tert-butyl methyl ether
TFA trifluoroacetic acid
For amino acid abbreviations see the table above.

If not mentioned otherwise, reactions are carried out at room temperature.

The synthesis of the compound A mentioned below is made in solution according to the following simplified scheme, more details are given below:

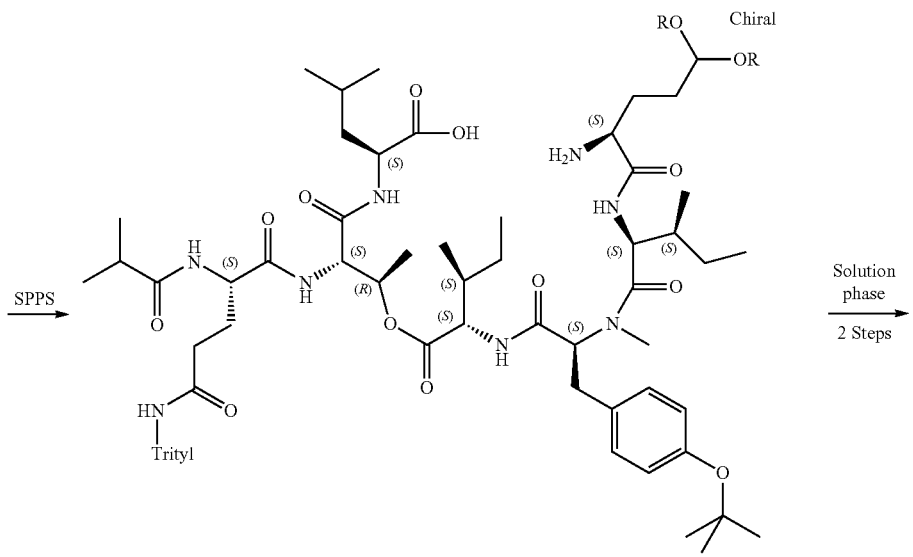

Compound 7 (R and R together form ethenyl ( —CH2CH2— )) or Compound 9 (each R is benzyl)

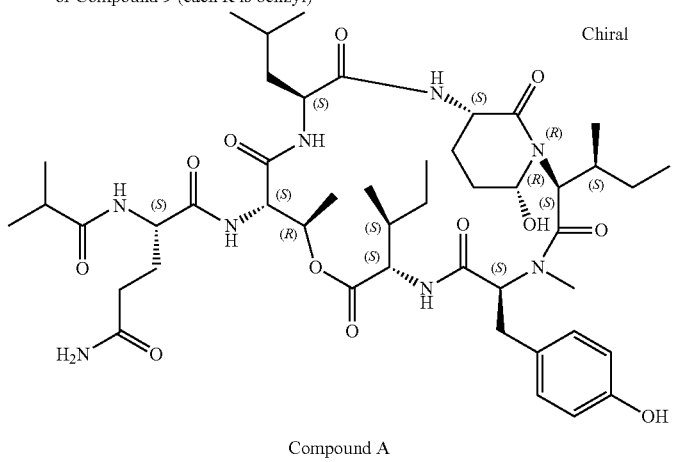

Compound A

The two steps in Solution phase are macrocylization and deprotection/equilibration. Details of this and preceding reactions are given in the following example:

The names of the compounds according to the 2004 IUPAC recommendations given in the reaction schemes and examples below are as follows:

Compound 1: benzyl (2S)-2-(dibenzylamino)-5-oxopentanoate;

Compound 2: benzyl (2S)-2-(dibenzylamino)-4-(1,3-dioxolan-2-yl)butanoate;

Compound 3: (2S)-2-(dibenzylamino)-4-(1,3-dioxolan-2-yl)butanoic acid;

Compound 4: (2S)-2-amino-4-(1,3-dioxolan-2-yl)butanoic acid;

Compound 5: (2S)-4-(1,3-dioxolan-2-yl)-2-{[(9H-fluoren-9-ylmethoxy)carbonyl]amino}-butanoic acid;

Compound 6: $N^2$-(2-methylpropanoyl)-$N^5$-(triphenylmethyl)-L-glutaminyl-O-{N-[(2S)-2-(dibenzylamino)-4-(1, 3-dioxolan-2-yl)butanoyl]-L-isoleucyl-O-(tert-butyl)-N-methyl-L-tyrosinyl-L-isoleucyl}-L-threonyl-L-leucine;

Compound 7: $N^2$-(2-methylpropanoyl)-$N^5$-(triphenylmethyl)-L-glutaminyl-O-{N-[(2S)-2-amino-4-(1,3-dioxolan-2-yl)butanoyl]-L-isoleucyl-O-(tert-butyl)-N-methyl-L-tyrosinyl-L-isoleucyl}-L-threonyl-L-leucine;

Compound 8: (2S)—N-[(3S,6S,9S,12S,15S,18S,19R)-3,9-di[(2S)-butan-2-yl]-6-{[4-(tert-butoxy)phenyl]methyl}-12-[2-(1,3-dioxolan-2-yl)ethyl]-7,19-dimethyl-15-(2-methylpropyl)-2,5,8,11,14,17-hexaoxo-1-oxa-4,7,10,13,16-pentaazacyclononadecan-18-yl]-2-(2-methylpropanamido)-N'-(triphenylmethyl)pentanediamide;

Compound 9: $N^2$-(2-methylpropanoyl)-$N^5$-(triphenylmethyl)-L-glutaminyl-O-{N-[(2S)-2-amino-5,5-bis(benzyloxy)pentanoyl]-L-isoleucyl-O-(tert-butyl)-N-methyl-L-tyrosinyl-L-isoleucyl}-L-threonyl-L-leucine;

Compound 10: (2S)—N-[(3S,6S,9S,12S,15S,18S,19R)-12-[3,3-bis(benzyloxy)propyl]-3,9-di[(2S)-butan-2-yl]-6-{[4-(tert-butoxy)phenyl]methyl}-7,19-dimethyl-15-(2-methylpropyl)-2,5,8,11,14,17-hexaoxo-1-oxa-4,7,10,13,16-pentaazacyclononadecan-18-yl]-2-(2-methylpropanamido)-N'(triphenylmethyl)pentanediamide;

Compound 12: 1,1'-[(3-bromopropane-1,1-diyl)bis(oxymethanediyl)]dibenzene;

Compound 13: 1,3-diethyl 2-acetamidopropanedioate;

Compound 14: 1,3-diethyl 2-acetamido-2-[3,3-bis(benzyloxy)propyl]propanedioate;

Compound 15: 2-acetamido-5,5-bis(benzyloxy)pentanoic acid;

Compound 16: (2S)-2-amino-5,5-bis(benzyloxy)pentanoic acid;

Compound 17: (2S)-5,5-bis(benzyloxy)-2-{[(9H-fluoren-9-ylmethoxy)carbonyl]amino}-pentanoic acid;

Compound A: (2S)—N-[(2S,5S,8S,11R,12S,15S,18S,21R)-2,8-di[(2S)-butan-2-yl]-21-hydroxy-5-[(4-hydroxyphenyl)methyl]-4,11-dimethyl-15-(2-methylpropyl)-3,6,9,13,16,22-hexaoxo-10-oxa-1,4,7,14,17-pentaazabicyclo[16.3.1]docosan-12-yl]-2-(2-methylpropanamido)pentanediamide.

Example 1

Synthesis of Compound A

1 A) Synthesis of Ethyleneglycol-Acetale Synthons Compound 3 and Compound 5

Reaction scheme 1

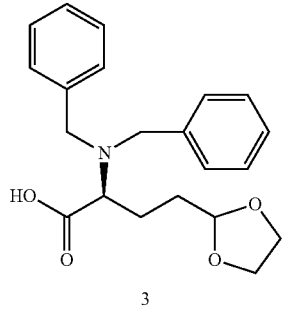

3

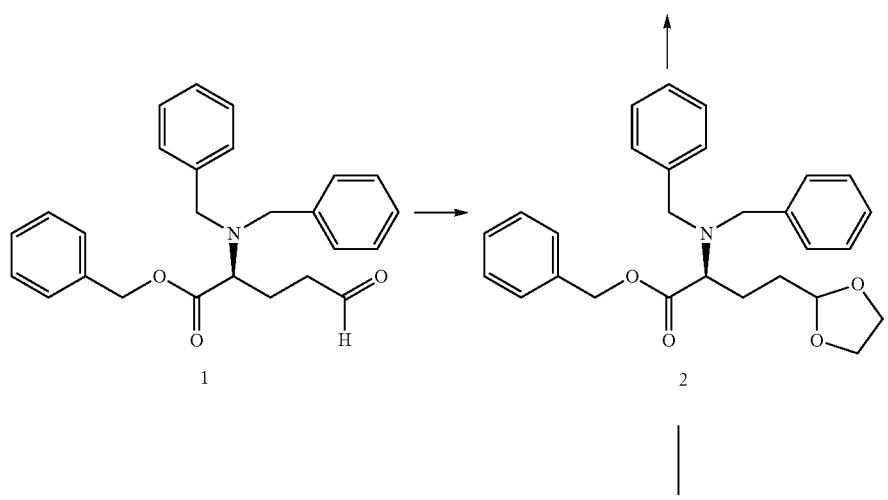

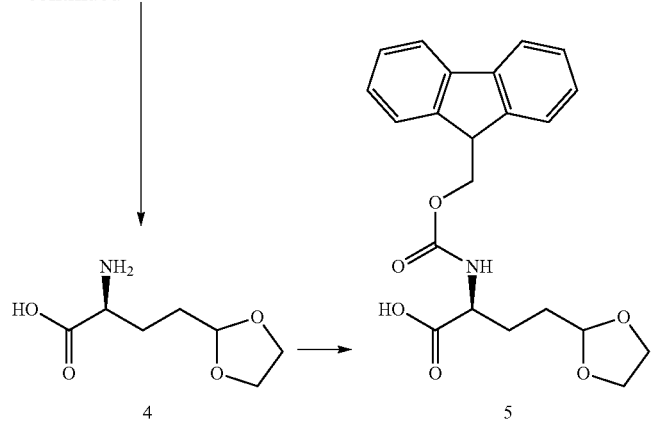

The unnatural amino acid with the ethyleneglycol-acetale protecting group was synthesized starting from the known aldehyde-intermediate 1 (scheme 1), which was prepared according to the procedures described in [Rodriguez and Taddei, Synthesis 2005, 3, pp. 493-495]. Aldehyde 1 was converted into the ethyleneglycol-acetale 2 by treating with ethyleneglycol in the presence of p-TsOH as catalyst and molecular sieves. The benzyl-ester in compound 2 was hydrolysed with LiOH to obtain the free acid compound 3, which was used for the preparation of the corresponding oligopeptide, compound 6. Alternatively, the benzyl-protecting groups in compound 2 were cleaved by hydrogenation using palladium on charcoal (10%) and the free amino-acid intermediate 4 was treated with commercially available Fmoc-HOSU ester to obtain the N-Fmoc-protected ethyleneglycol-acetale of the unnatural amino acid (compound 5). It is noteworthy to mention that no stability issues were faced with regard to stability of compounds 3 and 5. This stability cannot be taken granted in such a molecule comprising an acetale and a free carboxylic acid function.

a) Synthesis of Compound 2

To a solution of Compound 1 (29 g; 72.23 mmol) in DCM (700 mL) ethylene glycol (133 g, 2.14 moles), p-toluene-sulfonic acid monohydrate (15 g; 78.86 mmol) and molecular sieves (3 Angstrom, 40 g) were sequentially added. The reaction mixture was stirred for 18 h at room temperature. The molecular sieve was removed by filtration, the filter cake was washed with ethyl acetate and the filtrate was evaporated under reduced pressure. The residue was dissolved in ethyl acetate (1 L), extracted with water (3×300 mL) and the organic phase was evaporated under reduced pressure to obtain 33.3 g crude product. The crude product was purified by chromatography on silica gel with ethyl acetate/hexanes (4:6) to obtain 28.0 g of pure Compound 2 (87% yield).

1H-NMR of the product confirmed the proposed structure.
HR-MS: Calculated for $C_{28}H_{31}NO_4$ [M+H]+=446.23259. Found: 446.23248.

b) Synthesis of Compound 3

Compound 2 (26.8 g; 60.15 mmol) was dissolved in dioxane (250 mL). LiOH (10.1 g; 241.05 mmol) and water (150 mL) were added and the mixture was stirred for 72 h at room temperature. The formed suspension was treated with water (200 mL) and acetic acid (32 g) to obtain 2 clear phases. The biphasic mixture was diluted with ethyl acetate (500 mL) and the phases were separated. The aqueous phase was separated and was extracted with ethyl acetate (300 mL). The organic phases were combined and washed with water (300 mL). Evaporation of the solvent under reduced pressure gave 29 g crude product as a viscous liquid. The crude product was purified by flash chromatography on silica gel with DCM/isopropanol (9:1) as eluent to obtain 17.3 g product comprising ca. 10 mol % isopropanol according to 1H-NMR. Residual isopropanol was removed from the product by dissolving in isopropyl acetate (200 mL) and extraction of the isopropyl acetate solution with water (3×50 mL). Finally, the solvent was removed under reduced pressure and the product was dried in vacuo at 70° C. to obtain Compound 3 (16 g; 74.8% yield). 1H- and 13C-NMR Spectra of the product confirmed the proposed structure.

HR-MS: Calculated for $C_{21}H_{25}NO_4$ [M+H]+: 356.18564; [M+Na]+: 378.16758. Found: [M+H]+: 356.18586; [M+Na]+: 378.16748.

c) Synthesis of Compound 4 from Compound 3

Compound 3 (2.7 g; 7.596 mmol) was dissolved in isopropanol (60 mL) and the catalyst (10% Pd on charcoal; 300 mg) was added. The reaction mixture was hydrogenated for 23 h at room temperature under atmospheric pressure, after which time the hydrogenation was completed. The reaction mixture was diluted with water (60 mL) and stirred for 1 h at room temperature to dissolve the precipitated product. The reaction mixture was then filtered to remove the catalyst and the filter cake was washed with water/isopropanol (1:1) (45 mL). Evaporation of the solvent under reduced pressure and subsequent drying of the product in vacuo at 40° C. overnight gave compound 4 (1.24 g; 93.18% yield). 1H- and 13C-NMR-Spectra confirmed the proposed structure for compound 4.

HR-MS: Calculated for $C_7H_{13}NO_4$ [M+H]+: 176.09174; [M+Na]+: 198.07368. Found: [M+H]+: 176.09173; [M+Na]+: 198.07362.

d) Synthesis of Compound 4 from Compound 2

Compound 4 was prepared by hydrogenation of compound 2 using 10% palladium on charcoal as catalyst under atmospheric hydrogen pressure, in ethanol/water (1:1 v/v) as solvent at room temperature. For work-up, the catalyst was removed by filtration and the solvent was evaporated under reduced pressure. Subsequent drying of the product in vacuo at 45° C. gave compound 4 in quantitative yield.

The product was identical to compound 4 obtained from compound 3 above.

e) Synthesis of Compound 5

Compound 4 (1.2 g; 6.85 mmol) was dissolved in water (7 mL) and triethylamine (0.692 g) was added. To this stirred mixture, a solution of Fmoc-HOSU-Ester (=(9H-Fluoren-9-yl)methyl 2,5-dioxopyrrolidin-1-yl carbonate) (2.31 g; 6.85 mmol) in acetonitrile (6 g) was added and the reaction mixture was stirred for ca. 1 h at room temperature. The pH value of the resulting reaction mixture was adjusted to 8.5-9.0 by addition of triethylamine in several portions. In total, addition of ca. 0.7 g triethylamine was necessary to maintain a pH of 8.5-9.0. For work-up, the reaction mixture was subjected to flash chromatography on silica gel by direct transfer of the reaction mixture on a silica gel column. Elution with ethyl acetate/acetic acid (98:2), combination of product fractions and evaporation of the solvent gave wet compound 5. The wet product was suspended in hexanes, stirred for 1 h at room temperature and the precipitate was isolated by filtration. The precipitate was dried in vacuo at 50° C. over night to obtain a product comprising ca. 20 mol % of acetic acid. This product was dissolved in ethyl acetate (50 mL) at 60° C. and the solution was cooled down to room temperature. Seed crystals (compound 5) were added at room temperature and the suspension was stirred until a thin suspension was formed. The volume of the suspension was reduced to ca. 15 mL by partial evaporation of the solvent at 40° C. under reduced pressure, and hexanes (89 mL) was added to the suspension over 30 minutes at room temperature. The suspension was stirred for 1 additional h at room temperature and the product was isolated by filtration. The product was dried in vacuo at 50° C. overnight to obtain Compound 5 (2.31 g; 84.85% yield). HR-MS: Calculated for $C_{22}H_{23}NO_6$ $[M+H]^+$: 398.15982; $[M+NH_4]^+$:415.18636; $[M+Na]^+$: 420.14176. Found: $[M+H]^+$: 398.15991; $[M+NH_4]^+$:415.18655; $[M+Na]^+$: 420.14183.

$^1$H-NMR (600 MHz, $d_6$-DMSO): δ ppm 1.64 (2H, m); 1.68 (1H, m); 1.81 (1H, m); 3.76 (2H, m); 3.87 (2H, m); 3.98 (1H, m); 4.22 (1H, m); 4.27 (2H, m); 4.79 (1H, m); 7.33 (2H, t, J=7.3 Hz); 7.42 (2H, t, J=7.3 Hz); 7.66 (1H, d, J=8.1 Hz); 7.73 (2H, d, broad); 7.89 (2H, d, J=7.3 Hz); 12.59 (1H, s, broad).
$^{13}$C-NMR (150 MHz, $d_6$-DMSO): δ ppm 25.46 (CH2), 2993 (CH2), 46.67 (CH), 53.61 (CH), 64.27 (2×CH2), 65.65 (CH2), 103.12 (CH), 120.12 (2×CH), 125.30 (2×CH), 127.08 (2×CH), 127.67 (2×CH), 140.71 (2×C), 143.79 (2×C), 156.14 (C), 173.68 (C).
IR: 3345, 3321, 3063, 3021, 2974, 2963, 2949, 2767, 1950, 1914, 1878, 1741, 1691, 1682, 1610, 1541, 1525, 1477, 1464, 1451, 1403, 1367, 1323, 1285, 1270, 1249, 1225, 1188, 1138, 1104, 1087, 1055, 1033, 1008, 983, 963, 939, 925, 873, 836, 798, 782, 759, 740, 648, 622.

1 B) Synthesis of Compound 7 by SPPS

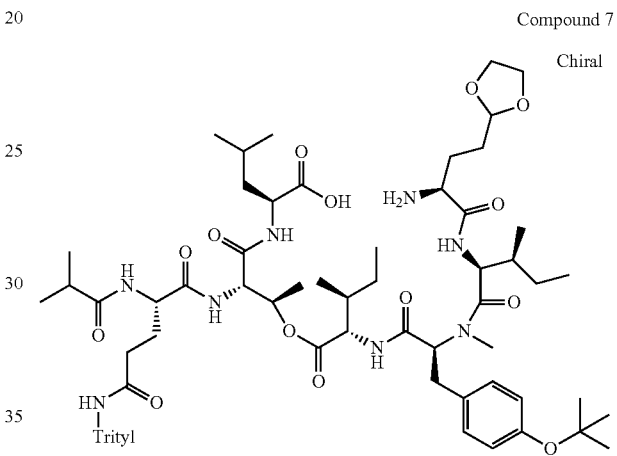

Compound 7

Compound 7 is synthesized by solid phase peptide synthesis (SPPS), the last steps being represented in short in the following simplified reaction scheme 2:

Reaction scheme 2

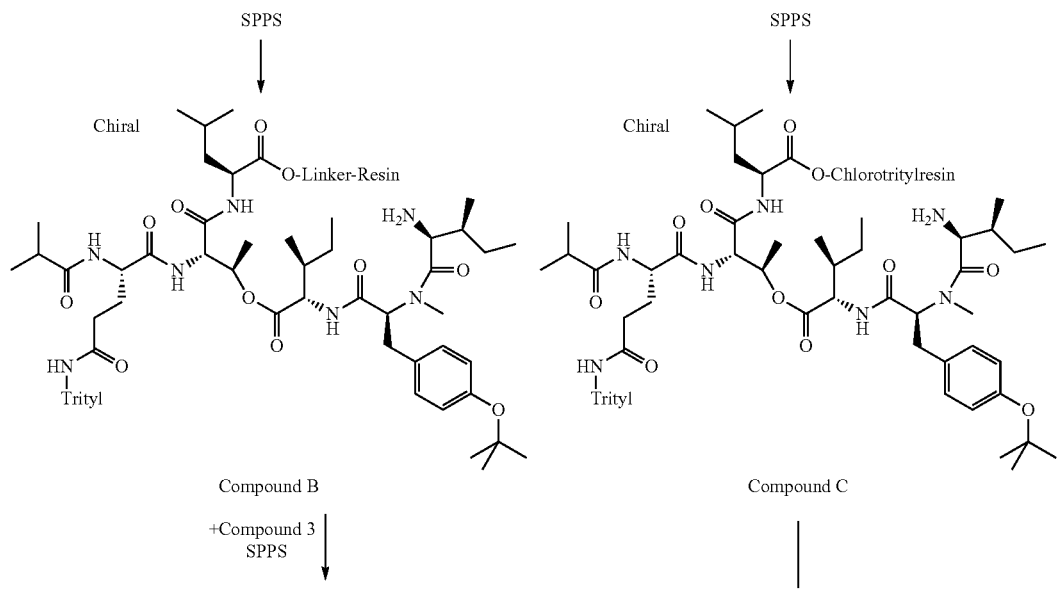

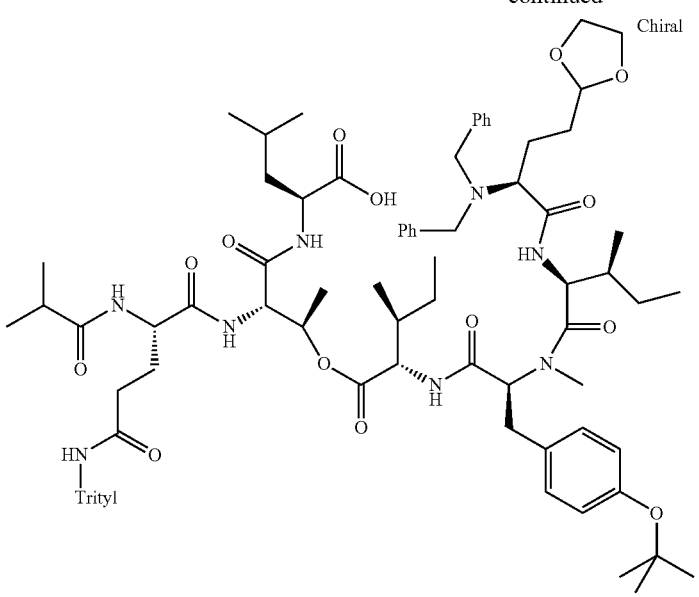

6

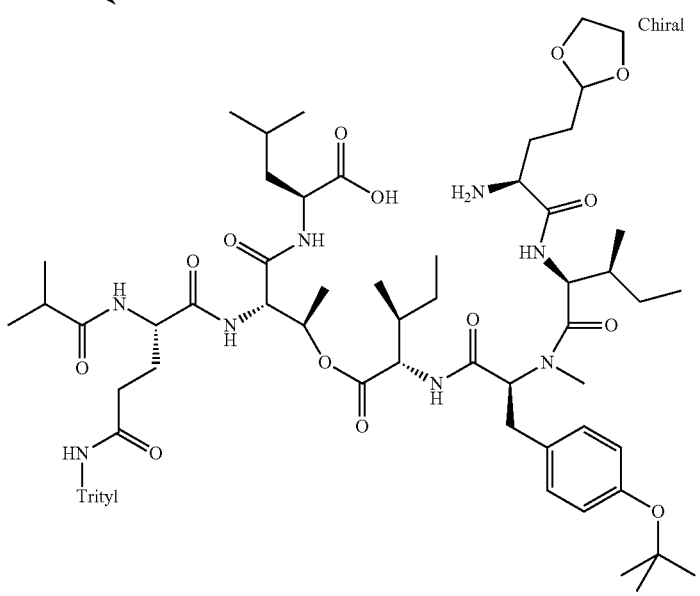

7

In alternative reactions, both the N-dibenzyl-protected compound 3, as well the N-Fmoc-protected compound 5 were used for the SPPS synthesis of the corresponding oligopeptides 6 and 7 respectively, comprising the unnatural amino acid with the aldehyde function, protected as ethylenegylcolacetale (scheme 2). The benzyl-protecting groups of compound 6 were removed by hydrogenation with palladium on charcoal (10%) in solution to obtain compound 7 (scheme 2). Alternatively, compound 7 was also obtained directly from SPPS on a chlorotrityl-resin, when compound 5 was used as synthon for the unnatural amino acid in the last coupling step. Surprisingly, no problems were faced with regard to stability of the acetal protecting group during SPPS and subsequent acid catalyzed cleavage of the oligopeptides 6 and 7 from solid support. Details are given below:

Equipment:

Peptide reactor with a filter cloth at the bottom. A nitrogen manifold allows to empty the reactor via filter cloth and bottom valve.

The linker-resin bound Compound B was manufactured as follows:

1 B) (A) Coupling of the Trityl-Linker to the Solid Support 200 g of Aminomethyl-polystyrene resin (crosslinked with 1% divinyl benzene, loading of aminomethyl groups 1 mmol/ g) (supplier: Senn Chemicals AG, Dielsdorf/Switzerland) were stirred alternatedly with several portions of dimethylformamide (1600 mL) and isopropanol (1600 mL) After two final washes with dimethlyformamide, the resin was treated with a previously prepared solution of 4-(diphenylhydroxymethyl)-benzoic acid (91.3 g, 300 mmol), 1-hydroxy-benzotriazole monohydrate (45.9 g, 300 mmol) and diisopropylcarbodiimide (75.7 g, 600 mmol) in dimethylformamide (1600 mL). The reaction mixture was stirred for 1.5 h and a Ninhydrin test was performed. The test still showed free amino groups and thus further diisopropylcarbodiimide (7.6 g, 60 mmol) was added and the reaction stirred overnight. A subsequent ninhydrin test in the morning was negative and the reaction mixture was filtered off. The resin was washed alternatingly with dimethylformamide and isopropanol. The resin was dried in vacuo and yielded 257 g of dry linker-resin. The material was used for the next synthesis step without further analysis.

1 B) (B) Coupling of Fmoc-Leu-OH

Preparation of Fmoc-Leu-Linker-Resin

Linker-Resin from the preceding step (190 g, 147.8 mmol) was swollen by stirring in toluene (1400 mL). The solvent was filtered off and replaced by a solution of toluene (1400 mL) and acetyl chloride (53 mL, 1478 mmol). This mixture was stirred for 2 h, filtered off, replaced by an identical mixture which was stirred for another 2 h before filtering off. The chlorinated resin was washed twice with toluene and three times with dichloromethane.

In a round bottom flask, a solution of Fmoc-Leu-OH (104.8 g, 296 mmol) and of N-methyl-morpholine (49 mL, 444 mmol) in dichloromethane (600 mL) was prepared. This solution was added to the resin and stirred overnight. In the morning, the solution was filtered of and the resin was washed with dichloromethane and isopropanol alternatingly. The resin was dried in vacuo and yielded 234.7 g of dry Fmoc-Leu-linker-Resin. The loading with Fmoc-groups was determined at 0.787 mmol/g what led to a yield of 185 mmol (125% of theory). Amino acid analysis at an external contractor confirmed <0.1% D-Leu antipode.

1 B) (C) Coupling of Fmoc-Thr-OH

Preparation of Fmoc-Thr-Leu-Linker-Resin

Fmoc-Leu-Linker-Resin from the preceding step (140 g, 109 mmol) was swollen by stirring in two successive portions of dimethylformamide (1100 mL) for 30 min each. Fmoc protecting group was cleaved by two subsequent washings of 20% piperidine in dimethylformamide for 5 min and 15 min respectively. The resin was washed by several alternating washes with dimethylfomamide and isopropanol. Phenolphtalein and water were added to a sample of the final wash solution. The absence of pink colour proofed successful removal of piperidine.

The resin was washed with tetrahydrofurane (1200 mL) three times to prepare for the following coupling step.

In a round bottomed flask a solution of Fmoc-Thr-OH (112.1 g, 328 mmol), hydroxylbenzotriazole monohydrate (51.25 g, 334 mmol) and diisopropylcarbodiimide (51 mL, 655 mmol) in tetrahydrofurane (600 mL) was prepared The solution was added to the resin and the pH checked immediately (pH=6.5). The reaction mixture was stirred for 1.5 h until a ninhydrin test showed complete reaction. The solution was filtered off and the resin was washed with dimethylformamide and isopropanol alternatingly. A small sample of the resin was dried and sent for amino acid analysis (0.13% D-Leu, <0.1% D-Thr, <0.1% L-allo-Thr, <0.1% D-allo-Thr), the bulk of the material was subjected to the next step without further drying.

1 B) (D) Coupling of Fmoc-Gln(Trt)-OH

Preparation of Fmoc-Gln(Trt)-Thr-Leu-Linker-Resin

The Fmoc-Thr-Leu-Linker-Resin from the previous step was swollen by stirring in two subsequent portions of dimethylformamide (1100 mL) for 30 min each.

Fmoc protecting group was cleaved by two subsequent washings with 20% piperidine in dimethylformamide for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottomed flask a solution of Fmoc-Gln(Trt)-OH (138.6 g, 226 mmol), HATU (86.2 g, 226 mmol) and ethyldiisopropylamine (58.4 g, 452 mmol) in dimethylformamide (400 mL) was prepared.

The solution was added to the resin and the pH checked immediately (pH=10). The reaction mixture was stirred for 3 h until a ninhydrin test showed complete reaction. The solution was filtered of and the resin was washed with dimethylformamide and isopropanol alternatingly.

The resin was dried in vacuo and yielded 170 g of dry Fmoc-Gln(Trt)-Thr-Leu-Linker-Resin. The loading with Fmoc-groups was determined at 0.60 mmol/g indicating a yield of 102 mmol (94% of theory over the last two steps). Amino acid analysis at an external contractor led to the following values: (0.13% D-Leu, <0.1% D-Thr, <0.1% L-allo-Thr, <0.1% D-allo-Thr, <0.8% D-Gln).

1 B) (E) Coupling of Isobutyric acid

Preparation of
Isobutyryl-Gln(Trt)-Thr-Leu-Linker-Resin

Fmoc-Gln(Trt)-Thr-Leu-Linker-Resin from the preceding step (169 g, 101 mmol) was swollen by stirring in two subsequent portions of dimethylformamide (1300 mL) for 30 min each.

Fmoc protecting group was cleaved by two subsequent washings with 20% piperidine in dimethylformamide (1300 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottom flask a solution of Isobutyric acid (17.9 g, 203 mmol), PyBOP (105.5 g, 203 mmol) and Ethyldiisopropylamine (52.4 g, 406 mmol) in dimethylformamide (550 mL) was prepared.

The solution was added to the resin and the pH checked immediately (pH=9.5). The reaction mixture was stirred for 2.5 h until a ninhydrin test showed complete reaction. The solution was filtered off and the resin was washed with dimethylformamide and isopropanol alternatingly.

The batch was directly subjected to the next step without drying and further analysis.

1 B) (F) Coupling of Fmoc-Ile-OH (Esterification)

Preparation of
Isobutyryl-Gln(Trt)-Thr(Ile-Fmoc)-Leu-Linker-Resin

Isobutyryl-Gln(Trt)-Thr-Leu-Linker-Resin (wet from preceding step, 101 mmol) was swollen by stirring in three subsequent portions of dichloromethane (1200 mL) for 20 min each.

The solvent was filtered off and MSNT (88 g, 297 mmol) and Fmoc-Ile-OH (105 g, 297 mmol) were added as solids. Dichloromethane (500 mL) was added as well as a solution of N-methyl imidazole (18.2 g, 223 mmol) and ethyldiisopropyamine (51.2 g, 396 mmol) in dichloromethane (100 mL) The reaction mixture was stirred for 2 h until HPLC in process control showed complete reaction. The solution was filtered off and the resin was washed with three portions of dichloromethane, three portions of dimethylformamide and three portions of isopropanol subsequently. The resin was dried in vacuo and yielded 172 g of dry Isobutyryl-Gln(Trt)-Thr(Ile-Fmoc)-Leu-Linker-Resin. Fmoc loading was determined to be 0.418 mmol/g thus indicating a yield of 72 mmol (71% over the last two steps).

1 B) (G) Coupling of Fmoc-N-methyl-Tyr(tBu)—OH

Preparation of Isobutyryl-Gln(Trt)-Thr(Ile-Tyr(tBu)
Me-Fmoc)-Leu-Linker-Resin

Isobutyryl-Gln(Trt)-Thr(Ile-Fmoc)-Leu-Linker-Resin from the preceding step (172 g, 72 mmol) was swollen by stirring in two subsequent portions of dimethylformamide (1300 mL) for 30 min each.

Fmoc protecting group was cleaved by two subsequent washings of 20% piperidine in dimethylformamide (1400 mL) for 5 min and 15 min respectively. The resin was washed by several alternating washes with dimethylfomamide and isopropanol. Phenolphtalein and water were added to a sample of the final wash solution. The absence of pink colour proofed successful removal of piperidine.

The resin was washed with dimethylformamide (1100 mL) three times to prepare for the following coupling step.

A solution of Fmoc-N-methyl-Tyr(tBu)—OH (68.7 g, 144 mmol) and HATU (55.1 g, 144 mmol) in dimethylformamide (700 mL) was prepared and added to the resin. Immediately after a solution of ethyldiisopropylamine (37.5 g 289 mmol) in dimethylformamide (100 mL) was added under stirring. pH checks immediately after addition of the coupling solution and after 1 h of reaction gave the same result (pH 10) The solution was stirred for 2 h until a ninhydrin test showed complete reaction. The solution was filtered of and the resin was washed with dimethylformamide and isopropanol alternatingly.

The batch was directly subjected to the next step without drying and further analysis.

1 B) (H) Coupling of Fmoc-Ile-OH

Preparation of Isobutyryl-Gln(Trt)-Thr(Ile-Tyr(tBu)
Me-Ile-Fmoc)-Leu-Linker-Resin (linker-resin bound
Compound B)

The wet Isobutyryl-Gln(Trt)-Thr(Ile-Tyr(tBu)Me-Fmoc)-Leu-Linker-Resin from the preceding step (72 mmol) was swollen by stirring in two subsequent portions of dimethylformamide (1200 mL and 1300 mL) for 30 min each. Fmoc protecting group was cleaved by two subsequent washings with 20% piperidine in dimethylformamide (1400 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (1100 mL) three times to prepare for the following coupling step.

In a round bottom flask a solution of Fmoc-Ile-OH (103.9 g, 294 mmol) COMU (125.9 g, 294 mmol) and Ethyldiisopropylamine (76 g, 588 mmol) in dichloromethane (440 mL) and dimethylformamide (440 mL) was prepared.

The solution was added to the resin and the reaction mixture stirred for 20 h. After that time a ninhydrin test was done, showing complete reaction. The solution was filtered off and the resin was washed with dimethylformamide and isopropanol alternatingly. The resin was dried in vacuo and yielded 185.5 g of dry Isobutyryl-Gln(Trt)-Thr(Ile-Tyr(tBu)Me-Ile-Fmoc)-Leu-Linker-Resin. The loading with Fmoc groups was determined to be 0.4 mmol/g. Thus a quantitative yield of 74 mmol resulted.

1 C) Solution Phase Synthesis of Compound 7

1 C) (A) Synthesis of Compound 6 a) Coupling of Compound 3 Isobutyryl-Gln(Trt)-Thr(Ile-Tyr(tBu)Me-Ile-Fmoc)-Leu-Linker-Resin from the previous step (10.4 g, 4.37 mmol) was swollen by stirring in two subsequent portions of dimethylformamide (50 mL) for 30 min each. The FMOC protecting group was cleaved by two subsequent treatments with 20% piperidine in dimethylformamide (50 mL) for 5 min and 15 min respectively. The resin was washed with several portions of dimethylformamide and isopropanol in an alternating sequence. Finally, the resin was washed with dimethylformamide (2×50 mL) to prepare for the next coupling step. In a 100 mL glass bottle, a solution of compound 3 (3.1 g, 8.74 mmol) PyBOP (4.55 g, 8.74 mmol) and ethyl-diisopropylamine (2.2 g, 17.0 mmol) in dimethylformamide (50 mL) was prepared. The basic solution (pH11) was agitated for 5 min before adding it to the resin. The reaction mixture was stirred for 3 h. Then the solution was filtered off and the resin was washed with dimethylformamide and isopropanol. Finally the resin was washed three times with dichloromethane (50 mL) to prepare for the cleavage of the peptide.

b) Cleavage from resin
To the wet peptide-resin obtained after coupling of compound 3 above, a mixture of acetic acid (40 mL) and dichloromethane (10 mL) was added and the suspension stirred for 5 h. The suspension was filtered and the filtrate collected in a round bottomed flask (filtrate 1). The resin was washed twice with dichloromethane (20 mL) and the washes were combined with filtrate 1. The resin was treated with a fresh portion of acetic acid (40 mL) and dichloromethane (10 mL) and the mixture was stirred overnight. The suspension was filtered and the filtrate collected in a round bottomed flask (filtrate 2). The resin was washed twice with dichloromethane (20 mL) and the washes combined with filtrate 2. All filtrates were combined and concentrated in a rotary evaporator. The residual acetic acid was removed by azeotropic distillation with toluene (100 mL). Complete evaporation of the solvent yielded 4.5 g of a glassy red-brown residue as crude product. The crude material was purified by RP-chromatography, using a YMC ODS-AQ column. The fractions were assessed using HPLC, rich fractions were concentrated in a rotary evaporator and the concentrate freeze dried. Yield: 2.86 g Compound 6 (44% for the last two steps).

HR-MS: Calculated for $C_{85}H_{112}N_8O_{14}$ $[M+H]^+$: 1469.83708. Found: 1469.83691

$^1$H-NMR-Spectrum confirmed the proposed structure.

1 C) (B) Synthesis of Compound 7 (Variant with Deprotection of Compound 6)

Compound 6 (0.5 g, 0.34 mmol) was dissolved in isopropanol/water (95:5 v/v, 15 mL) and the solution was flushed with argon. Palladium on charcoal (10% Pd; 0.25 g) was added under a stream of argon and the suspension was heated to IT 35-40° C. Hydrogen gas was introduced into the gas phase and the mixture was stirred under atmospheric pressure of hydrogen, until an IPC(HPLC) indicated the completion of the reaction (<5% starting material).

For work-up, the catalyst was removed by filtration and the filter residue was washed with isopropanol. The filtrate was evaporated to obtain 500 mg crude product. The crude product was purified by flash chromatography on silica gel using ethyl acetate/methanol (93:7) to obtain 348 mg compound 7. Yield: 79.3%.

HR-MS: Calculated for $C_{71}H_{100}N_8O_{14}$ $[M+H]^+$: 1289.74318; $[M+Na]^+$:1311.72512. Found: $[M+H]^+$: 1289.74308; $[M+Na]^+$:1311.72487.

1 D) SPPS Synthesis of Compound 7 (Variant with Coupling of Compound 5)

The Chlortritylresin bound Compound C was manufactured and used as follows:

1 D) (A): Coupling of Fmoc-Leu-OH to Chlortrityl-resin—Preparation of Fmoc-Leu-Chlortritylresin Chlor-(2'-chlor)trityl-polystyrene resin (47.15 g, 50 mmol) was swollen by stirring in dichloromethane (350 mL) over night. The solvent was filtered off and replaced by a solution of dichloromethane (330 mL) and acetyl chloride (19.75 g, 250 mmol). This mixture was stirred for 3 h 45 min, filtered off and replaced by an identical mixture which was stirred for another 90 min before filtering off. This treatment was repeated once again for 1 h 45 min. The chlorinated resin was washed three times with dichloromethane.

In a round bottom flask, a solution of Fmoc-Leu-OH (35.4 g, 100 mmol) and of N-methyl-morpholine (15.2 g, 150 mmol) in dichloromethane (120 mL) was prepared. This solution was added to the resin and stirred overnight. In the morning, the solution was filtered off and the resin was washed with dichloromethane and isopropanol alternatingly. The resin was dried in vacuum and yielded 69.1 g of dry Fmoc-Leu-Chlortritylresin. The loading with Fmoc-groups was determined at 0.74 mmol/g what led to a yield of 51 mmol (quantitative yield).

1 D) (B): Coupling of Fmoc-Thr-OH—Preparation of Fmoc-Thr-Leu-Chlortritylresin Fmoc-Leu-Chlortritylresin from the preceding step (67.1 g, 49.7 mmol) was swollen by stirring in two successive portions of dimethylformamide (400 mL and 350 mL) for 30 min and 75 min respectively.

Fmoc protecting group was cleaved by two subsequent washings of 20% piperidine in dimethylformamide for 5 min and 15 min respectively. The resin was washed by several alternating washes with dimethylformamide and isopropanol. Phenolphthalein and water were added to a sample of the final wash solution. The absence of pink colour proofed successful removal of piperidine.

The resin was washed with tetrahydrofurane (330 mL) three times to prepare for the following coupling step.

In a round bottomed flask a solution of Fmoc-Thr-OH (33.95 g, 99.4 mmol), hydroxylbenzotriazole monohydrate (23.31 g, 152 mmol) and diisopropylcarbodiimide (37.6 g, 298 mmol) in tetrahydrofurane (285 mL) was prepared The solution was added to the resin and the reaction mixture stirred overnight. HPLC showed complete reaction. The solution was filtered off and the resin was washed with dimethylformamide and isopropanol alternatingly. Finally the resin was washed 5 times with TBME, dried in vacuum and yielded 67.5 g of dry Fmoc-Thr-Leu-Chlortritylresin. The loading with Fmoc-groups was determined at 0.58 mmol/g leading to a yield of 39 mmol (79% of theory).

1 D) (C): Coupling of Fmoc-Gln(Trt)-OH—Preparation of Fmoc-Gln(Trt)-Thr-Leu-Chlortritylresin Fmoc-Thr-Leu-Chlortritylresin (49.4 g, 28.7 mmol) from the previous step was swollen by stirring in two subsequent portions of dimethylformamide (350 mL each) for 30 min and 70 min respectively.

Fmoc protecting group was cleaved by two subsequent washings with 20% piperidine in dimethylformamide for 5 min and 15 min respectively. The resin was washed by several alternating washes with dimethylfomamide and isopropanol. Phenolphthalein and water were added to a sample of the final wash solution. The absence of pink colour proved successful removal of piperidine.

The resin was washed with dimethylformamide (250 mL) three times to prepare for the following coupling step.

In a round bottomed flask a solution of Fmoc-Gln(Trt)-OH (34.4 g, 57.3 mmol), HATU (21.5 g, 57.3 mmol) and ethyldiisopropylamine (14.8 g, 114.6 mmol) in dimethylformamide (190m L) was prepared.

The solution was added to the resin and the pH checked immediately (pH=>8). The reaction mixture was stirred for 2 h 30 min before HPLC in process control showed complete reaction. The solution was filtered off and the resin was washed with dimethylformamide and isopropanol alternatingly.

The resin was not dried but directly introduced into the next step.

1 D) (D): Isobutyrylation—Preparation of Isobutyryl-Gln(Trt)-Thr-Leu-Chlortrityl-resin Fmoc-Gln(Trt)-Thr-Leu-Chlortritylresin (wet from preceding step, 28.7 mmol) was washed with dimethylformamide (300 mL) for 30 min.

Fmoc protecting group was cleaved by two subsequent washings with 20% piperidine in dimethylformamide (400 mL) for 5 min and 15 min respectively. The resin was washed by several alternating washes with dimethylfomamide and isopropanol. Phenolphtalein and water were added to a sample of the final wash solution. The absence of pink colour proved successful removal of piperidine.

The resin was washed with dimethylformamide (250 mL) three times to prepare for the following coupling step.

In a round bottom flask a solution of Isobutyric acid (5.01 g, 56.9 mmol), PyBOP (29.33 g, 56.4 mmol) and Ethyldiisopropylamine (15.55, 120 mmol) in dimethylformamide (190 mL) was prepared.

The solution was added to the resin and the pH checked immediately (pH=11). The reaction mixture was stirred for 1 h before HPLC in process control showed complete reaction. The solution was filtered off and the resin was washed with dimethylformamide and isopropanol alternatingly.

The batch was directly subjected to the next step without drying and further analysis.

1 D) (E): Coupling of Fmoc-Ile-OH (esterification)—Preparation of Isobutyryl-Gln(Trt)-Thr(Ile-Fmoc)-Leu-Chlortritylresin Isobutyryl-Gln(Trt)-Thr-Leu-Chlortritylresin (wet from preceding step, 28.7 mmol) was washed with two portions of dichloromethane at room temperature and two additional portions of cold (0° C.) dichloromethane under nitrogen.

In a round bottom flask a solution of Fmoc-Ile-OH (37.65 g, 106.5 mmol) N-methyl imidazole (10.00 g, 121.8 mmol) and MSNT (31.65 g, 106.8 mmol) in MED (210 mL) was prepared at 0° C. under nitrogen. The coupling solution was added to the cold resin and the reaction mixture was stirred for 30 min before an additional amount of N-methyl imidazole (5.33 g, 64.9 mmol) was added. The reaction was stirred for further 30 min before HPLC in process control showed complete reaction. The solution was filtered off and the resin was washed with dimethylformamide isopropanol alternatingly. Finally the resin was washed 5 times with TBME, dried in vacuum and yielded 55.7 g of dry Isobutyryl-Gln(Trt)-Thr(Ile-Fmoc)-Leu-Chlortritylresin. Fmoc loading was determined to be 0.43 mmol/g leading to a yield of 24.2 mmol (84% over the last three steps).

1 D) (F): Coupling of Fmoc-N-Me-Tyr(tBu)—OH—Preparation of Isobutyryl-Gln(Trt)-Thr(Ile-Tyr(tBu)Me-Fmoc)-Leu-Chlortritylresin Dry Isobutyryl-Gln(Trt)-Thr(Ile-Fmoc)-Leu-Chlortritylresin from the preceding step (55.5 g, 24.1 mmol) was swollen by stirring in two subsequent portions of dimethylformamide (400 mL each) for 30 min each.

Fmoc protecting group was cleaved by two subsequent washings of 20% piperidine in dimethylformamide (450 mL) for 5 min and 15 min respectively. The resin was washed by several alternating washes with dimethylformamide and isopropanol. Phenolphtalein and water were added to a sample of the final wash solution. The absence of pink colour proofed successful removal of piperidine.

The resin was washed with dimethylformamide (280 mL) three times to prepare for the following coupling step.

A solution of Fmoc-N-methyl-Tyr(tBu)—OH (22.12 g, 47.7 mmol) and HATU (17.81 g, 46.8 mmol) and ethyldiisopropylamine (12.09 g 93.5 mmol) in dimethylformamide (280 mL) was prepared and added to the resin. The pH of the reaction mixture was checked immediately after addition of the coupling solution (pH>8) The solution was stirred for 2 h before HPLC in process control showed complete reaction. The solution was filtered off and the resin was washed with dimethylformamide and isopropanol alternatingly.

The batch was directly subjected to the next step without drying and further analysis.

1 D) (G): Coupling of Fmoc-Ile-OH—Preparation of Isobutyryl-Gln(Trt)-Thr(Ile-Tyr(tBu)Me-Ile-Fmoc)-Leu-Chlortritylresin The wet Isobutyryl-Gln(Trt)-Thr(Ile-Tyr(tBu)Me-Fmoc)-Leu-Chlortritylresin from preceding step, (24.1 mmol) was washed with dimethylformamide (400 mL) for 30 min. Fmoc protecting group was cleaved by two subsequent washings with 20% piperidine in dimethylformamide (450 mL) for 5 min and 15 min respectively. The resin was washed by several alternating washes with dimethylformamide and isopropanol. Phenolphthalein and water were added to a sample of the final wash solution. The absence of pink colour proved successful removal of piperidine.

The resin was washed with dimethylformamide (280 mL) three times to prepare for the following coupling step.

In a round bottom flask a solution of Fmoc-Ile-OH (33.01, 93.4 mmol) COMU (39.99 g, 93.4 mmol) and Ethyldiisopropylamine (24.16 g, 187 mmol) in dichloromethane (110 mL) and dimethylformamide (110 mL) was prepared.

The solution was added to the resin and the pH checked (pH>8). The reaction mixture was stirred for 2 h. After that time HPLC in process control showed complete reaction. The solution was filtered off and the resin was washed with dimethylformamide and isopropanol alternatingly. Finally the resin was washed 5 times with TBME. The resin was dried in vacuum and yielded 61.1 g of dry Isobutyryl-Gln(Trt)-Thr(Ile-Tyr(tBu)Me-Ile-Fmoc)-Leu-Chlortritylresin. The loading with Fmoc groups was determined to be 0.30 mmol/g. Thus a yield of 18.3 mmol resulted, corresponding to 76% over the last two steps.

1 D) (H) Coupling of Compound 5: Preparation of Compound 7 a) Coupling

Isobutyryl-Gln(Trt)-Thr(Ile-Tyr(tBu)Me-Ile-Fmoc)-Leu-Chlortritylresin (6.5 g, 1.89 mmol) was swollen by stirring in two subsequent portions of dimethylformamide (45 mL and 40 mL) for 30 min each.

The FMOC protecting group was cleaved by two subsequent treatments with 20% piperidine in dimethylformamide (50 mL and 55 mL) for 5 min and 15 min respectively. The resin was washed with several portions of dimethylformamide and isopropanol in an alternating sequence. A color test with phenolphthalein/water confirmed absence of base. Finally, the resin was washed with dimethylformamide (3×30 mL) to prepare for the following coupling step.

In a round bottom flask, a solution of compound 5 (1.50 g, 3.77 mmol) PyBOP (1.96 g, 3.77 mmol) and ethyl-diisopropylamine (0.98 g, 7.54 mmol) in dimethylformamide (20 mL) was prepared. The basic solution (pH8) was agitated for 5 min before adding it to the resin. The reaction mixture was stirred for 2 h and the progress of the reaction was monitored by cleaving a sample from the resin. HPLC of the sample showed complete conversion. The solution was filtered off and the resin was washed with dimethylformamide and isopropanol in an alternating sequence. From the dimethylformamide wet resin, the FMOC protecting group was cleaved by two subsequent treatments with 20% piperidine in dimethylformamide (60 mL) for 5 min and 15 min respectively. The resin was washed with several portions of dimethylformamide and isopropanol in an alternating sequence.

The effectiveness of washing was checked with phenolphthalein/water. Finally the resin was washed three times with dichloromethane (40 mL) to prepare for the cleavage of the peptide.

b) Cleavage from Resin

To the wet Isobutyryl-Gln(Trt)-Thr(Ile-Tyr(tBu)Me-Ile-Compound 5-H)-Leu-Linker-Resin a mixture of dichloromethane (40 mL), acetic acid (4.99 mL) and trifluoroethanol (4.96 mL) were added and the suspension was stirred for 3 h. The suspension was filtered and the filtrate collected in a round bottomed flask. The cleavage step was repeated twice with identical amounts of cleavage cocktail for 2 h each time. All filtrates where combined. The resin was washed three times with toluene (40 mL) and the washes combined with the filtrates.

The solution containing the product was evaporated to dryness in a rotary evaporator.

The residual solid was dissolved in acetonitrile/water and freeze dried. 2.95 g of lyophilized powder was isolated as crude product.

The crude material was purified by RP-chromatography, using a Kromasil RP 4 10 um column (Eka Chemicals AB, Bohus, Sweden). The fractions were assessed using HPLC, product-rich fractions were combined and concentrated in a rotary evaporator and the concentrate was freeze dried to obtain 1.0 g compound 7 (41% yield for the last two steps). Purity: 92% a.

$^1$H-NMR spectrum of the product confirmed the proposed structure as a mixture of rotamers.

HR-MS: Calculated for $C_{71}H_{100}N_8O_{14}$ [M+H]$^+$: 1289.74318; [M+Na]$^+$:1311.72512. Found: [M+H]$^+$: 1289.74292; [M+Na]$^+$:1311.72473.

1 E) Synthesis of Compound A

The final steps in the synthesis are shown in the subsequent scheme:

Reaction scheme 3:

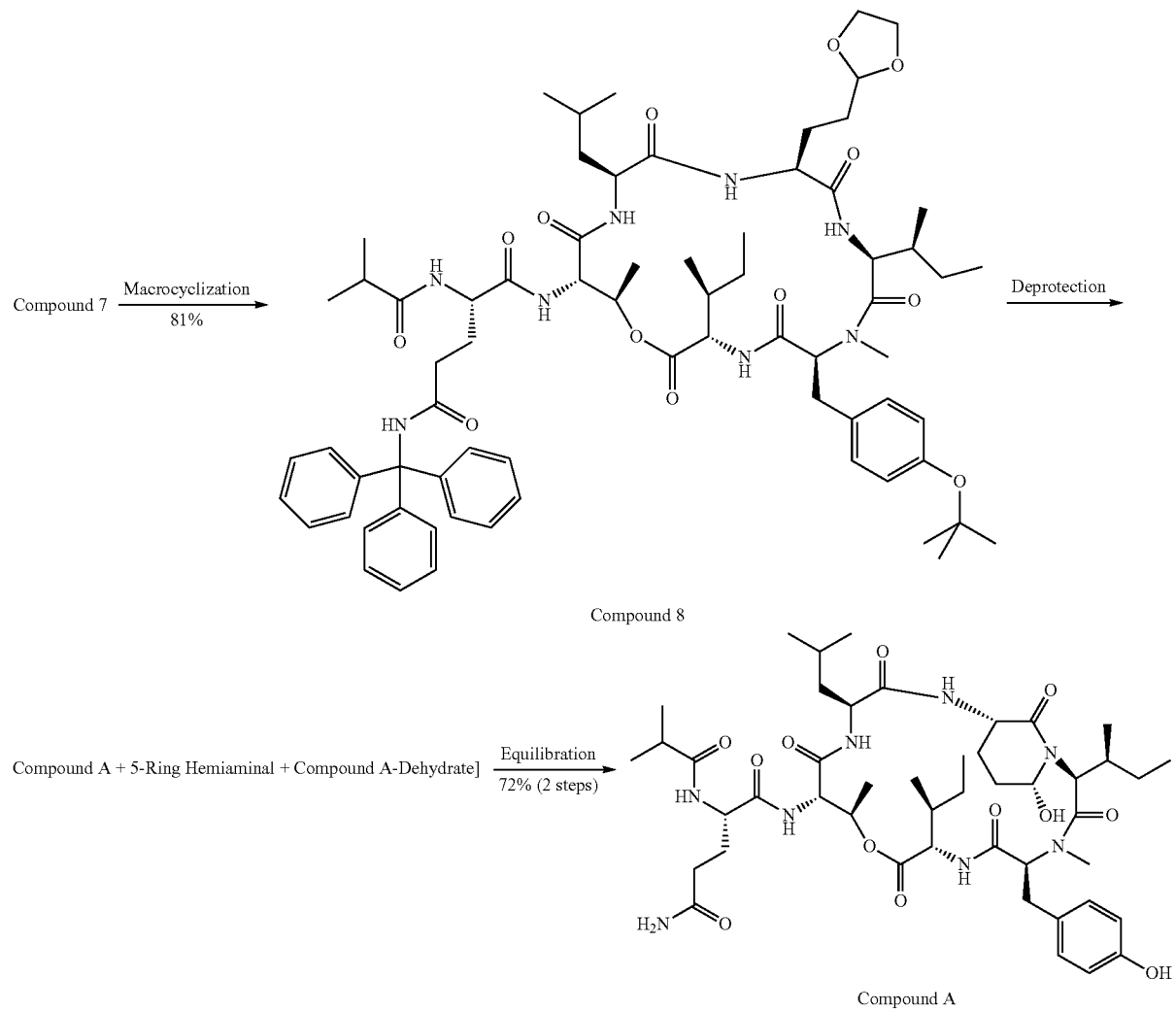

Compound 8

Compound A

In detail the synthesis is described in the following:

1 E) (A) Macrocyclization: Preparation of Compound 8

4-DMAP (100 mg, 0.82 mmol) and HATU (205.4 mg, 0.54 mmol) were dissolved in acetonitrile (15 mL). The solution was cooled to 0° C. To this solution, a solution of compound 7 (348 mg, 0.27 mmol) in acetonitrile (20 mL) was added dropwise within 10 minutes. The reaction mixture was stirred for additional 10 minutes at 0° C. to complete the cyclization. For work-up, the reaction mixture was poured onto water (50 mL) and isopropyl acetate (150 mL) was added, followed by the addition of brine (10 mL). The phases were separated, and the organic phase was extracted again with a dilute aqueous NaCl-solution (60 mL). The organic phase was separated and the solvent was evaporated in rotavap under reduced pressure to obtain 523 mg crude product. The crude product was purified by flash chromatography on silica gel with ethyl acetate as mobile phase to obtain 278.9 mg compound 8 (81.3% yield).

HR-MS: Calculated for $C_{71}H_{98}N_8O_{13}$ $[M+H]^+$: 1271.73261; $[M+NH_4]+$: 1288.75916; $[M+Na]^+$: 1293.71456. Found: $[M+H]^+$: 1271.73210; $[M+NH_4]^+$: 1288.75820; $[M+Na]^+$: 1293.71478.

$^1$H-NMR (600 MHz, $d_6$-DMSO): δ ppm 0.47 (3H, m); 0.73 (3H, m); 0.75-0.87 (12H, m); 0.97-1.05 (8H, m); 1.10 (3H, m); 1.13 (1H, m); 1.25 (9H, m); 1.33 (1H, m); 1.46 (1H, m); 1.56 (6H, m); 1.65 (2H, m); 1.79 (1H, m); 1.96 (1H, m); 2.30 (2H, m); 2.43 (1H, m); 2.68 (4H, m); 3.29 (1H, m); 3.73-3.88 (4H, m); 4.17 (1H, m); 4.19 (1H, m); 4.24 (1H, m); 4.30 (1H, m); 4.42 (1H, m); 4.57 (1H, m); 4.73 (1H, m); 5.17 (1H, m); 5.26 (1H, m); 6.86 (2H, m); 7.12-7.27 (18H, m); 7.90 (1H, m); 7.94 (1H, m); 8.18 (1H, m); 8.51 (2H, m); 8.82 (1H, m).

IR: 3637, 3400, 3306, 3059, 3031, 2968, 2934, 2877, 1738, 1658, 1509, 1469, 1449, 1414, 1388, 1367, 1339, 1239, 1162, 1100, 1066, 1037, 968, 946, 851, 767, 753, 741, 702, 637, 625.

1 E) (B) Deprotection and Equilibration

Compound 8 (200 mg, 0.157 mmol) was dissolved in dichloromethane (40 mL) and the solution was cooled to 0° C. Trifluoroacetic acid (11.5 g) was added dropwise to the solution at 0° C. and the reaction mixture was stirred for additional 3 h at 0° C. The reaction mixture was then diluted with dichloromethane (40 mL) and water (2 mL) was added. The reaction temperature was elevated to 20-25° C. and the mixture was stirred for 16 h at this temperature. The reaction mixture was then poured onto a solution of sodium acetate (16.3 g) in water (80 mL) and ethyl acetate (40 mL) was added. The biphasic mixture was stirred intensively and the phases were separated. The organic phase was washed with water (2×20 mL) and the water phases were extracted with ethyl acetate (40 mL). The organic phases were combined and dried over magnesium sulfate. Evaporation of the solvent at 40-45° C. under reduced pressure gave 270 mg of crude product. The crude product was purified by flash chromatography on silica gel using ethyl acetate/isopropanol (9:1) as eluent to obtain 105 mg of compound A. Yield: 71.8%.

The structure was confirmed by NMR data.

HR-MS: Calculated for $C_{46}H_{72}N_8O_{12}$ $[M+H]^+$: 929.53425; $[M+NH_4]^+$: 946.56080; $[M+Na]^+$: 951.51619. Found: $[M+H]^+$: 929.53412; $[M+NH_4]^+$: 946.56110; $[M+Na]^+$: 951.51611.

Example 2

Synthesis of Compound a Using an Acyclic Acetal Protecting Group: Employing of the Dibenzyl Acetale The following reaction scheme shows the use of compound 9 as an alternative to Compound 7 in Example 1:

Reaction scheme 4:

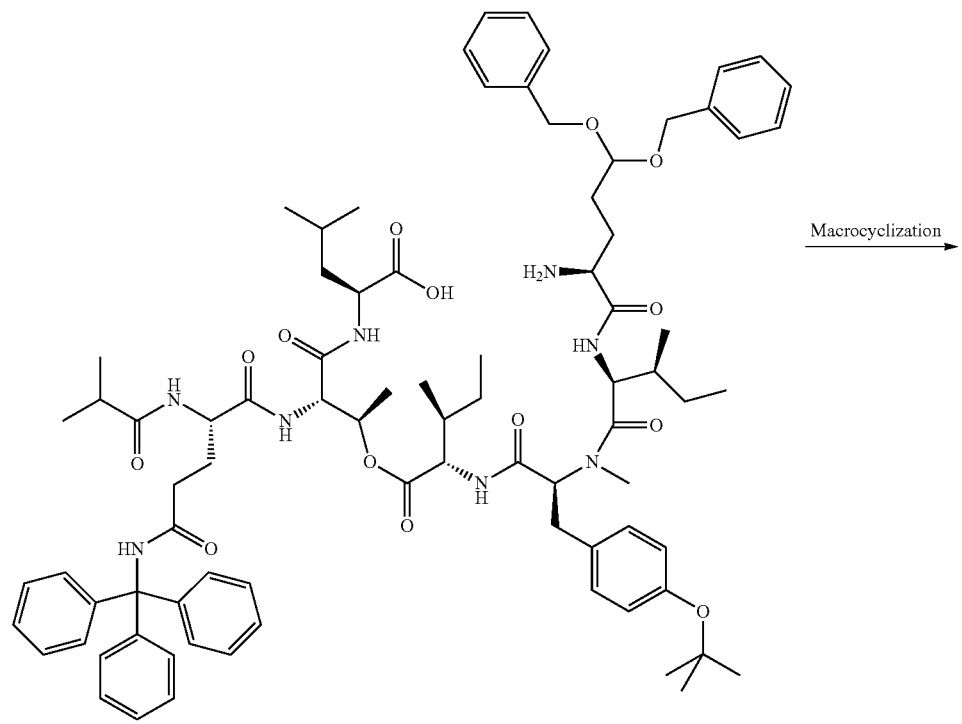

Compound 9

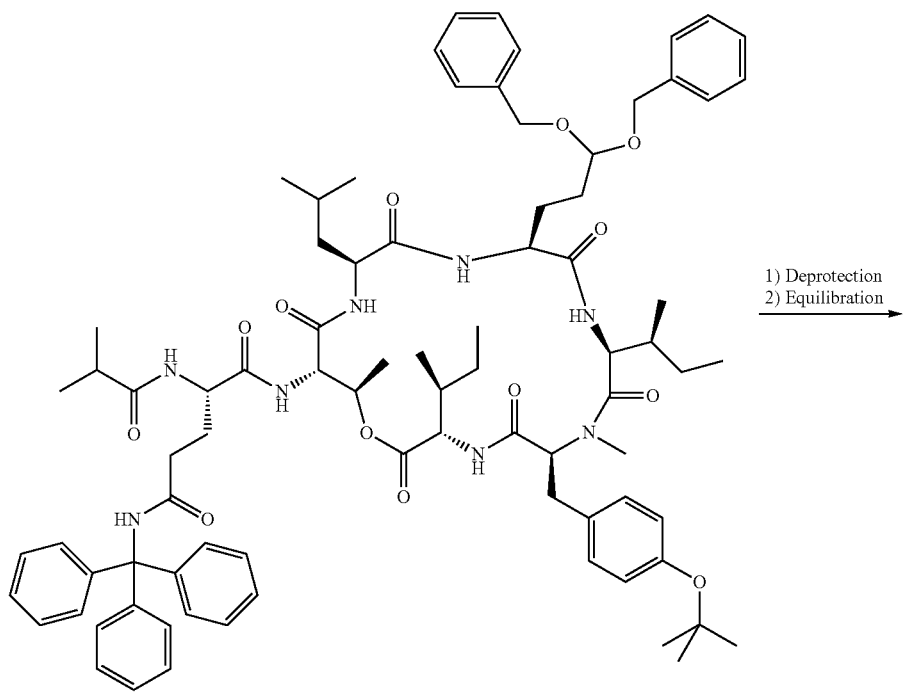
Compound 10
1) Deprotection
2) Equilibration →
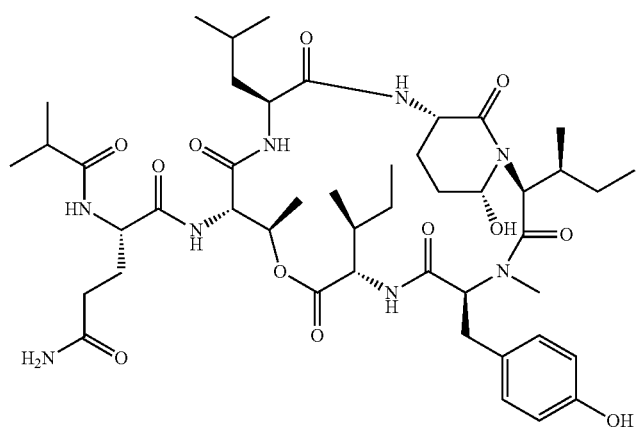
Compound A
In detail, the corresponding precursors and the reactions in the scheme are realized as follows:
2 a) Synthesis of the Dibenzyl-Acetale Synthon (Compound 17)
Compound 17 was prepared according to the synthesis scheme shown below:
Reaction scheme 5:
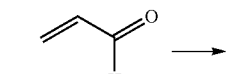
11 (Acrolein)

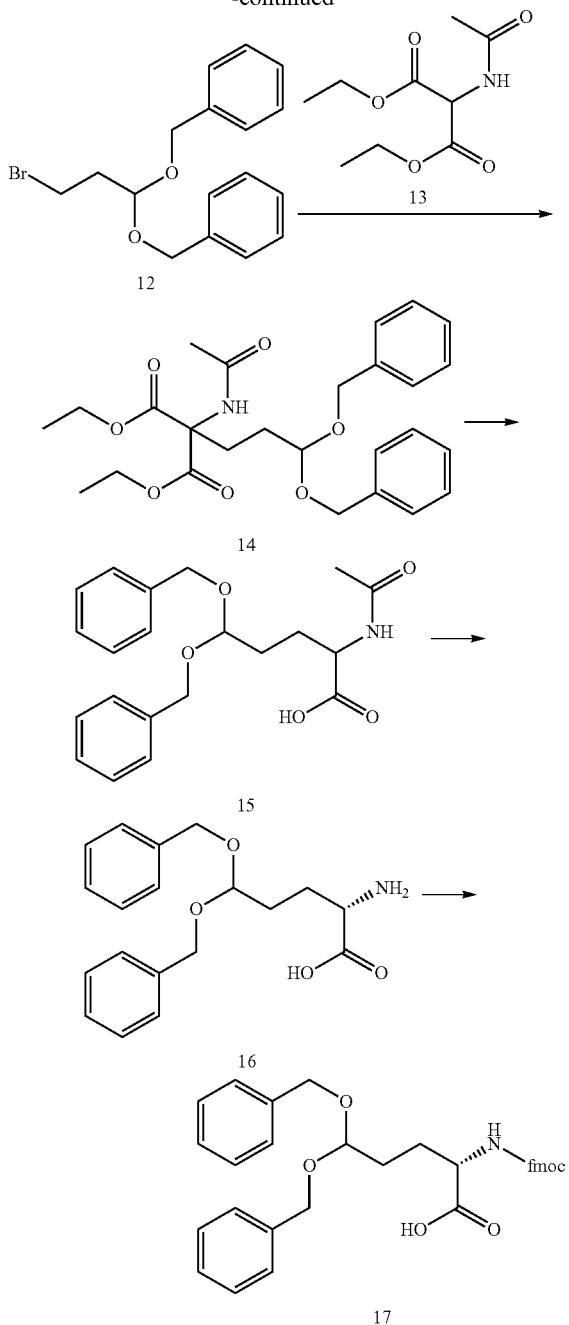

2 B) Synthesis of Compound 12

In a 3 L-reactor under nitrogen at 0° C., dried acrolein (105.3 g, 1.78 mol) in methylene chloride (1.15 kg) was introduced Trimethylbromosilane (281.7 g, 1.78 mol) was added dropwise over 30 min with a dropping funnel, keeping the temperature below 5° C. After 1 h 30 min of stirring, benzyl alcohol (311.1 g, 2.85 mol) was added dropwise over 45 min, and the mixture was stirred at 0° C. for 16 h. To the orange solution, pyridine (29 g, 0.36 mol), acetic anhydride (38 g, 0.36 mol) and DMAP (4.4 g, 0.04 mol) were added. The mixture was stirred at room temperature for 24 h, cooled to 10° C., and NaHCO₃ 10% solution (750 mL) was added until pH=7. The organic layer was washed with water (2×500 mL), and dried over anhydrous sodium sulfate. Evaporation of the solvent gave Compound 12 (428 g, 90%) as a crude yellow oil which dissociates upon standing a few hours in the fridge. After removal of the viscous orange lower phase, 6% of benzyl acetate was still present in the crude material.

$^1$H NMR (400 MHz, CDCl$_3$) δ ppm 2.2 (q, 2H), 3.4 (t, 2H), 4.5 (d, 2H), 4.6 (d, 2H), 4.9 (t, 1H), 7.2 (m, 10H).

2 C) Synthesis of Compound 14

In a 3 L-reactor, diethylacetamidomalonate (Compound 13, 275 g, 1.241 mol) was introduced in anhydrous DMF (800 g) under N$_2$. Potassium tert-butoxide (144 g, 1.241 mol) dissolved in anhydrous DMF (424 g) was added over 10 min. by a dropping funnel. The temperature rose to 45° C. The mixture was heated up to 80° C., and crude Compound 12 (428 g, 1.034 mol) was added dropwise over 1 h. Additional DMF (125 g) was used, and the mixture was stirred for 2 h at 80° C. under inert atmosphere. The solvent was then evaporated. Ethyl acetate (1.2 L) and water (2.5 L) were added. The organic layer was washed with aq. NaCl 10% (3×1.5 L), and the organic solvent was distilled off.

Crystallization of the residue, containing some residual ethyl acetate, from t-butyl-methyl ether/heptane gave Compound 14 in 87% yield as a white solid (423 g, purity: 97%).

$^1$H NMR (400 MHz, CDCl$_3$) δ ppm 1.2 (t, 6H), 1.6 (m, 2H), 2.0 (s, 3H), 2.5 (m, 2H), 4.2 (m, 1H), 4.55 (d, 2H), 4.65 (d, 2H), 4.7 (t, 1H), 6.8 (s, 1H), 7.3 (m, 10H).

2 D) Synthesis of Compound 15

In the 3 L-reactor, Compound 14 (211 g, 434 mmol) and 950 mL ethanol 95% were introduced. Potassium hydroxide (30 g, 477 mmol) in 150 mL ethanol 95% was added over 25 min with a dropping funnel. The slurry became a clear solution. The mixture was stirred for 3 h 30 min at RT. The complete conversion of the monoacid/monoester intermediate was established by HPLC. The mixture was heated to reflux for 2 h 30 min for decarboxylation. Then, more potassium hydroxide (34 g, 564 mmol) in 150 mL ethanol 95% was added, and the mixture was stirred for 2 h at 75° C. The ethanol was then distilled off over 1 h. The mixture was cooled to room temperature; water was added, followed by t-butyl-methyl-ether to extract insoluble by-products. Then, the aqueous layer was acidified with acetic acid to pH 5.0. and the product was extracted again with t-butyl-methyl-ether, the organic layer was washed with water, and concentrated in vacuo. Note that a mild concentration is required, more precisely a temperature below 50° C., with a good vacuum, and quite fast; otherwise decomposition to the cyclic derivative occurs. The recovered oil crystallizes very quickly. Recrystallization from t-butyl-methyl-ether/Heptane (1:2) gave 148.6 g of Compound 15 as a white solid (yield: 87%, purity: 98% a).

$^1$H NMR (400 MHz, CDCl$_3$) δ ppm 1.8 (s, 3H), 1.9 (m, 2H), 2.0 (m, 2H), 4.5 (q, 1H), 4.6 (d, 2H), 4.7 (d, 2H), 4.8 (t, 1H), 6.4 (d, 1H), 7.3 (m, 10H).

2 E) Synthesis of Compound 16

In a 3 L-reactor citrate buffer (1 L, pH=5) was introduced. The aminoacid, Compound 15 (146 g, 385 mmol) was added, and the pH was adjusted to 8.0-8.5 with sodium hydroxide 30% (84 g) and additional citrate buffer (130 mL). Cobalt chloride 1 mM (150 mL) was added to get a concentration of cofactor of 0.1 mM. The enzyme (acylase "Amano" ACV12502 (Amano Enzyme Inc., Nagoya, Japan), 7.25 g, 5% w/w) was finally added at 30° C. The brown mixture was stirred until HPLC showed 50% conversion (around 24 h). The white slurry was acidified to pH 7.0, filtered off. Note that filtration of the crude solid was quite slow and required a large funnel to proceed properly. The solid was washed with water (3×) and acetone (3×), and eventually dried in vacuo. Recrystallisation in methanol/water gives 51.6 g of Compound 16 as a white solid (41% isolated yield, purity: 99%). mp 190° C. with decomposition.

$^1$H NMR (400 MHz, CDCl$_3$) δ ppm 1.8 (m, 4H), 2.5 (s, 2H), 3.1 (t, 1H), 4.5 (d, 2H), 4.6 (d, 2H), 4.7 (t, 1H), 7.3 (m, 10H).

2 F) Synthesis of Compound 17

In a 750 mL-reactor, under inert atmosphere, was introduced Compound 16 (40.2 g, 120 mmol) in water (320 mL) and acetonitrile (80 mL). To this white slurry was added over 35 min triethylamine (24.3 g, 240 mmol). After complete dissolution of the solid, Fmoc-OSu (40.5 g, 120 mmol) was added. The mixture was stirred at room temperature for 3 h 30. Extraction was carried out with ethylacetate. The organic layer was washed with water, and a large amount of solvent was distilled off. A small amount of water was added, and the mixture was acidified to pH 4.6. The organic layer was kept, washed with water (2×) and finally concentrated in vacuo. Recrystallization of the residue in t-butyl-methyl-ether/Heptane (⅓) gave Compound 17 as a white solid (58.2 g, 88% yield, purity: 92% a, ee: 100% established by chiral HPLC).

$^1$H NMR (400 MHz, DMSO) δ ppm 1.8 (m, 4H), 4.0 (m, 1H), 4.2 (q, 1H), 4.3 (d, 2H), 4.5 (d, 2H), 4.6 (d, 2H), 4.8 (t, 1H), 7.3 (m, 11H), 7.4 (d, 2H), 7.6 (d, 1H), 7.7 (d, 2H), 7.9 (d, 2H).

2 G) Synthesis of Compound 9

Compound 17 (8.388 g, 15.21 mmol) was coupled on Isobutyryl-Gln(Trt)-Thr(Ile-Tyr(tBu)Me-Ile-Fmoc)-Leu-Linker-Resin (10.3 g, 4.33 mmol), the Fmoc protecting group was cleaved on the linker-resin-bound peptide and the product was cleaved from the linker-resin according to the procedures described above for the preparation of compound 6. The crude product was purified by RP-chromatography, using a YMC-ODS AQ column. The fractions were assessed using HPLC, product-rich fractions were combined and concentrated in a rotary evaporator and the concentrate was freeze dried to obtain 2.3 g of compound 9 (36.8% yield for the last two steps). HPLC-Purity: 92.9% a.

$^1$H-NMR confirmed the proposed structure as a mixture of rotamers.

HR-MS: Calculated for $C_{83}H_{111}N_8O_{14}$ [M+H]$^+$: 1443.82143. Found: [M+H]$^+$: 1443.82166.

2 H) Synthesis of Compound 10 (Macrocyclization)

4-DMAP (256 mg, 2.09 mmol) and HATU (527 mg, 1.39 mmol) are dissolved in acetonitrile (20 mL). The solution is cooled to 0° C. To this solution, a solution of compound 9 (1.00 g, 0.693 mmol) in acetonitrile (30 mL) is added dropwise within 10 minutes. The reaction mixture is stirred for additional 15 minutes at 0° C. to complete the cyclization. For work-up, the reaction mixture is poured onto water (100 mL) and isopropyl acetate (250 mL) is added, followed by the addition of brine (20 mL). The phases are separated and the organic phase is extracted again with a dilute aqueous NaCl-solution (60 mL). The organic phase is dried over anhydrous magnesium sulfate and the solvent is evaporated at 40-45° C. under reduced pressure to obtain 1.08 g crude product. Purification of the crude product by flash chromatography on silica gel using ethyl acetate as eluent and drying of the product in vacuo at 40-45° C. gave 0.62 g compound 10.

HR-MS: Calculated for $C_{83}H_{108}N_8O_{13}$ [M+H]$^+$: 1425.81086; [M+NH$_4$]$^+$: 1442.83741; [M+Na]$^+$: 1447.79281; [M+K]$^+$: 1463.76675. Found: [M+H]$^+$: 1425.81140; [M+NH$_4$]$^+$: 1442.83728; [M+Na]$^+$: 1447.79248; [M+K]$^+$: 1463.76685.

$^1$H-NMR (600 MHz, d$_6$-DMSO): δ ppm 0.47 (br. S., 1H), 0.47-0.54 (m, 1H), 0.63-0-70 (m, 2H), 0.73-0.81 (m, 9H), 0.85 (d, J=6.6 Hz, 3H), 0.97-1.05 (m, 7H), 1.08 (d, J=6.6 Hz, 2H), 1.16-1.22 (m, 2H), 1.23-1.31 (m, 3H), 1.27 (m, 9H), 1.46-1.52 (m, 1H), 1.53-1.61 (m, 3H), 1.65-1.73 (m, 3H), 1.80-1.88 (m, 2H), 1.94-2.01 (m, 1H), 2.00 (s, 1H), 2.32 (m, 2H), 2.39-2.47 (m, 1H), 2.49-2.55 (m, 2H), 2.68-2.76 (m, 1H), 2.72 (s, 2H), 3.29 (dd, J=14.3, 7.7 Hz, 1H), 3.36 (m, 8H). 4.20-4.24 (m, 1H), 4.30-4.34 (m, 1H), 4.48-4.56 (m, 3H), 4.58-4.66 (m, 3H), 4.71 (m, 1H), 5.27-5.35 (m, 1H), 6.84-6.91 (m, 2H), 7.15-7.22 (m, 11H), 7.25-7.31 (m, 8H), 7.32-7.36 (m, 6H), 7.90-7.98 (m, 2H), 8.52 (s, 1H), 8.74-8.83 (m, 1H).

2 I) Synthesis of Compound A from Compound 10 (De-Protection and Equilibration)

Compound 10 (400 mg, 0.281 mmol) is dissolved in dichloromethane (80 mL) and the solution is cooled down to 0° C. Trifluoroacetic acid (20.5 g) is added under intense stirring at 0° C. The reaction mixture is stirred for additional 3 h at this temperature and diluted with dichloromethane (80 mL), followed by the addition of water (4.0 mL). The temperature was then allowed to rise to room temperature and the reaction was stirred intensively for 20 h at room temperature.

The reaction mixture is then poured onto a solution of sodium acetate (29.3 g) in water (160 mL) and ethyl acetate (80 mL) is added. The biphasic mixture is stirred intensively and the phases are separated. The organic phase is washed with water (2×40 mL) and the water phases are extracted with ethyl acetate (80 mL). The organic phases are combined and dried over magnesium sulfate. Evaporation of the solvent at 40-45° C. under reduced pressure gave 520 mg of crude product. The crude product was purified by flash chromatography on silica gel using ethyl acetate/isopropanol (9:1) as eluent to obtain 171 mg of Compound A. Yield: 65.5%.

NMR and HR-MS data confirmed the proposed structure.

HR-MS: Calculated for $C_{46}H_{72}N_8O_{12}$ [M+H]$^+$: 929.53425; [M-FNH$_4$]$^+$: 946.56080; [M+Na]$^+$: 951.51619. Found: [M+H]$^+$: 929.53345; [M+NH$_4$]$^+$: 946.56045; [M+Na]$^+$: 951.51536.

Example 3

Shift of Equilibrium

A possible side reaction of the acetal cleavage and formation of ahp may result in the dehydrate form of Compound A. This can be converted easily (back) into Compound A using a simple procedure for hydration of the dehydrate form depicted in the following reaction scheme:

Reaction scheme 6:

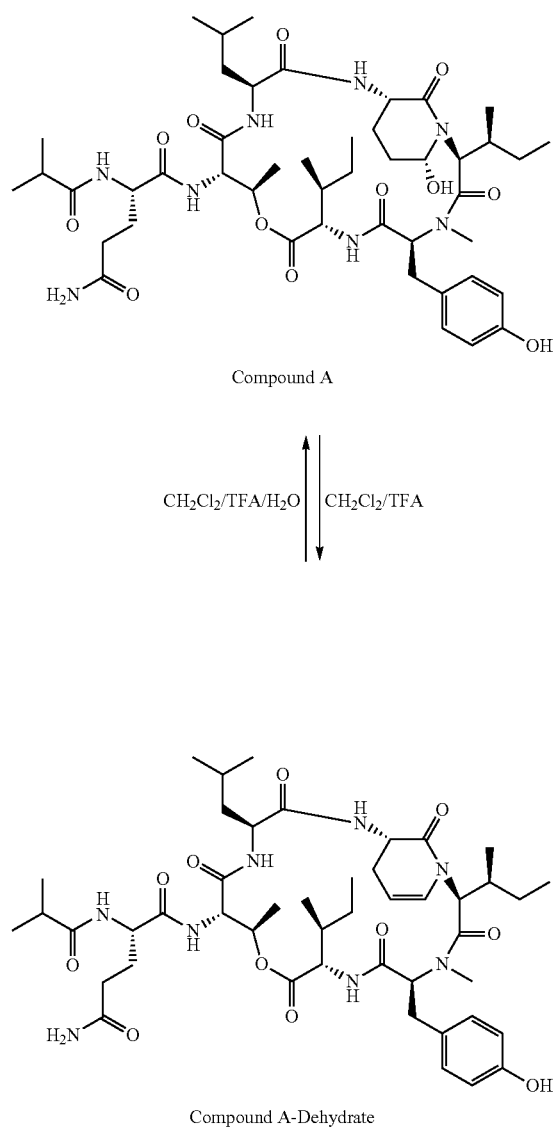

This allows to improve the yield of Compound A in any type of synthesis (be it chemical as in the present disclosure or by use of fermentation as in WO2009/024527).

For example, during cleavage of acid sensitive protecting groups in a compound comprising the ahp-subunit, e.g. Compound A in the Scheme before Example 1, the formation of large amounts of the corresponding dehydrated byproduct (Compound A-Dehydrate) is observed. This byproduct is usually separated e.g. by chromatography and disposed. This leads to loss of valuable product and to low yield for this step. For example, if the deprotection product(s) of Compound 8 are subjected to acidic conditions to cleave the trityl- and t-butyl protecting groups (scheme 4), significant amounts of Compound-A-Dehydrate are formed as byproduct. Depending on the acid concentration and reaction conditions, Compound-A-Dehydrate might be formed even as major product in this product mixture.

For example, a ratio Compound A/Compound A-Dehydrate (1:2) was observed when trifluoroacetic acid/dichloromethane (5:95 v/v) was used to cleave the protecting groups after the oxidation step (Example 1E(B)).

It was therefore searched for ways to convert the dehydrate byproduct into the desired product. It has now been found that this can be achieved by acid catalyzed equilibration of the product mixture in the presence of water under well-defined conditions. Addition of water to the reaction mixture of example 1 and subsequent stirring at room temperature for 19 h gave a product mixture with a ratio Compound A/Compound A-Dehydrate of ca. 96:4. Thus, addition of water to the reaction mixture after the acid-catalyzed de-protection step (scheme 4) changed the ratio of Compound A/Compound A-Dehydrate from (1:2) under water free conditions to (96:4) after water addition and equilibration.

The formation of Compound A-Dehydrate from Compound A under acidic deprotection conditions was confirmed by conversion of pure Compound A into Compound A—Dehydrate using trifluoroacetic acid in DCM. Treatment of Compound A with 33% (v/v) TFA in DCM for 2 h at room temperature gave a product mixture of Compound A-Dehydrate/Compound A in a ratio of 78:22 according to HPLC. The dehydration could be driven to >95% conversion, when water absorbing agents, such as molecular sieves were added to the reaction mixture. Thus, stirring of pure Compound A in a 1:2 mixture of TFA/DCM in the presence of molecular sieves gave the dehydrated-product in quantitative crude yield and ca. 96 area % HPLC purity (example 3B). There were still ca. 4 area-% of Compound A present in the crude product.

Conversion of Compound A-Dehydrate from Example 3B into Compound A was demonstrated by stirring Compound A-dehydrate in dichloromethane in the presence of trifluoroacetic acid and water (Example 3C). The product thus obtained comprised 95.6 area % Compound A and only 4.4 area % Compound A-dehydrate according to HPLC.

Reaction scheme 7:

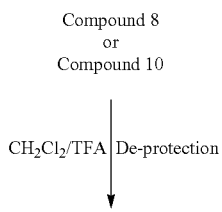

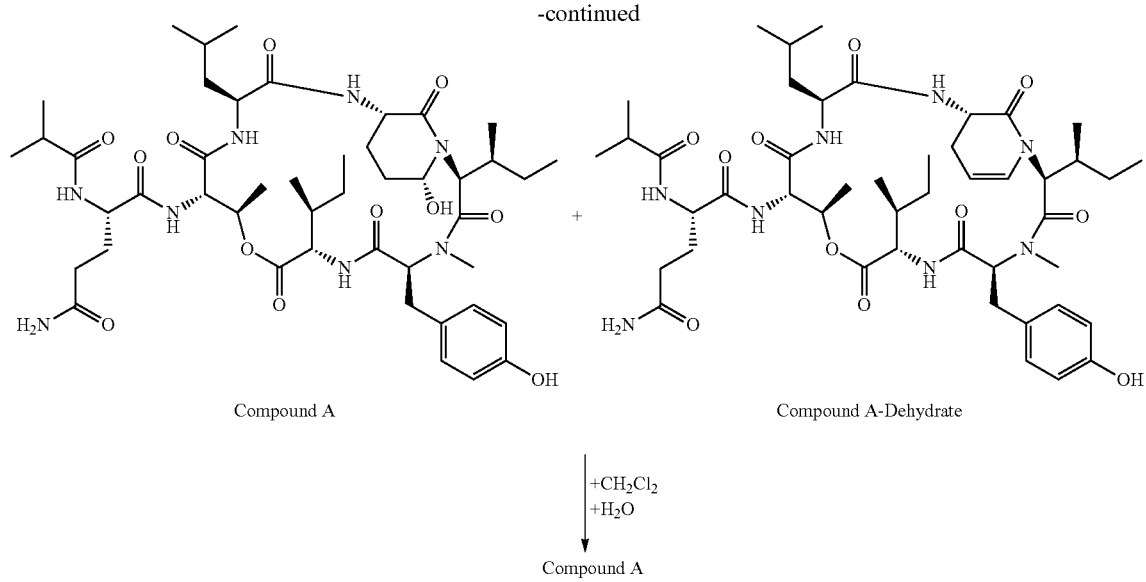

Compound A       +       Compound A-Dehydrate

|+CH$_2$Cl$_2$
|+H$_2$O
↓

Compound A

For physical data of Compound A see Examples 1E(B) and 2 I).

The equilibration also converts the 5-ring hemiaminal isomer into compound A, which is a 6-ring hemiaminal. The 5-ring hemiaminal isomer is formed in large amounts as kinetic product after de-protection of the aldehyde function (reaction scheme 3). This isomer is converted to the thermodynamically more stable compound A during equilibration.

What is claimed is:

1. A process for the preparation of a cyclic depsipeptide compound of the formula I,

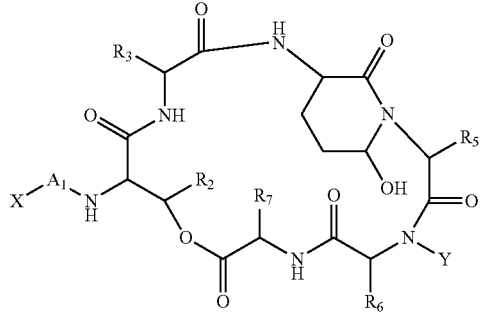

wherein
$A_1$ is a bivalent moiety of an amino acid with a terminal carboxy or carbamoyl group and is bound at its right hand side in formula I via a carbonyl to the rest of the molecule; or is $C_{1-8}$-alkanoyl or phosphorylated hydroxy-$C_{1-8}$-alkanoyl;
X is bound via an N of $A_1$ and is acyl, or is absent if $A_1$ is $C_{1-8}$-alkanoyl or phosphorylated hydroxy-Cl_8-alkanoyl;
$R_2$ is $C_{1-8}$-alkyl;
$R_3$ is the side chain of an amino acid;
$R_5$ is the side chain of an amino acid;
$R_6$ is the side chain of a hydroxy amino acid;
$R_7$ is the side chain of an amino acid; and
Y is hydrogen or $C_{1-8}$-alkyl;
or a salt thereof,
said process comprising
deprotecting a compound of the formula II

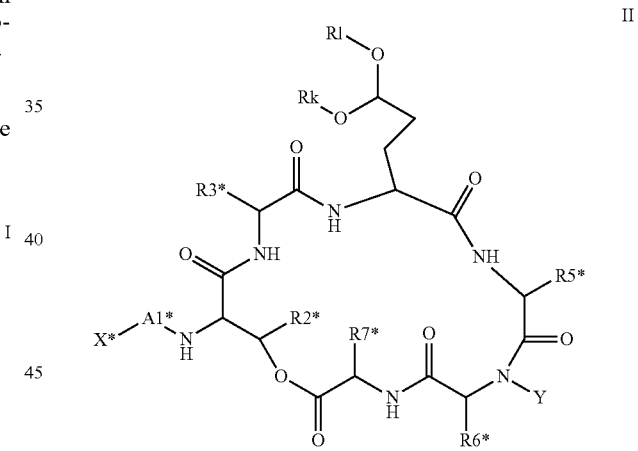

wherein the aldehyde protecting group(s) Rk and Rl are independently of each other unsubstituted or substituted alkyl or together with the two binding O atoms and the carbon atom to which the two O atoms are bound form a ring that is unsubstituted or substituted, Y is as defined for a compound of the formula I and X*, $A_1$*, $R_2$*, $R_3$*, $R_5$*, $R_6$*, and $R_7$* correspond to X, $A_1$, $R_2$, $R_3$, $R_5$, $R_6$, and $R_7$ in formula I, respectively, but with the proviso that reactive functional groups on these moieties are present in protected form at least if they could participate in undesired side reactions, to result in a compound of the formula I;
and, if desired, converting a free compound of the formula I into a salt, a salt of a compound of the formula I into a different salt of a compound of the formula I, or into the free compound of the formula I, and/or converting a dehydrate analogue and/or five ring analogue of a compound of the formula I into the corresponding compound of the formula I.

2. The process according to claim 1, comprising manufacturing the compound of the formula II by a combination of Solid Phase Peptide Synthesis and Solution Phase synthesis from the corresponding starting amino acids and side chain precursors.

3. The process according to claim 1, comprising, for the synthesis of the compound of the formula II given in claim 1, cyclization under lactamization of a linear, not yet cyclic, precursor peptide of the compound of the formula II, carrying an N-terminal amino group and a C-terminal carboxy group, under reaction conditions that allow for the formation of an amide bond from said amino and said carboxy group.

4. The process according to claim 3, where the linear precursor peptide is of the formula III,

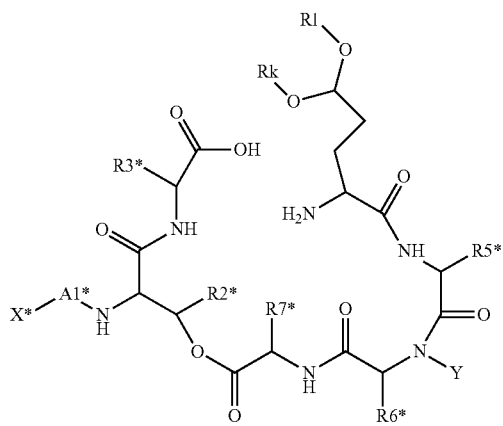

III wherein Rk, Rl, X*, $A_1^*$, $R_2^*$, $R_3^*$, $R_5^*$, $R_6^*$ and $R_7^*$ are as defined for a compound of the formula II in claim 1, which can be obtained directly from solid phase peptide synthesis or by deprotection from the corresponding compound of the formula III*,

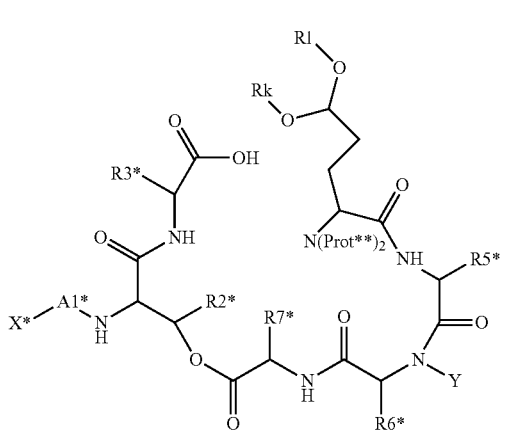

III* wherein Rk, Rl, X*, $A_1^*$, $R_2^*$, $R_3^*$, $R_5^*$, $R_6^*$ and $R_7^*$ are as defined for a compound of the formula II above and wherein each of the Prot** moieties is a protecting group that can be removed under conditions different from those of the cleaving reaction to yield the compound of formula III, by deprotecting the protected amine.

5. The process according to claim 4, further comprising, for the synthesis of the compound of the formula III, or of a compound of the formula III*, cleaving a compound of the formula IV,

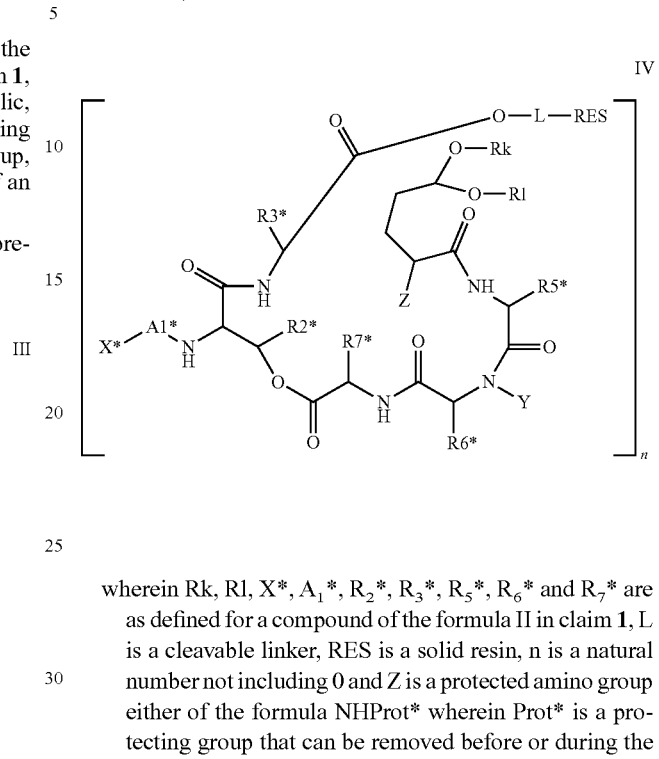

IV wherein Rk, Rl, X*, $A_1^*$, $R_2^*$, $R_3^*$, $R_5^*$, $R_6^*$ and $R_7^*$ are as defined for a compound of the formula II in claim 1, L is a cleavable linker, RES is a solid resin, n is a natural number not including 0 and Z is a protected amino group either of the formula NHProt* wherein Prot* is a protecting group that can be removed before or during the cleaving reaction or further subsequently to it to yield a compound of the formula III; or Z is a protected amino group of the formula N(Prot)$_2$ wherein each one of Prot is an amino protecting group that can be removed under conditions different from those of the cleaving reaction to yield the compound of the formula III*.

6. The process according to claim 5, further comprising, for the synthesis of the compound of the formula IV, coupling an amino acid of the formula V,

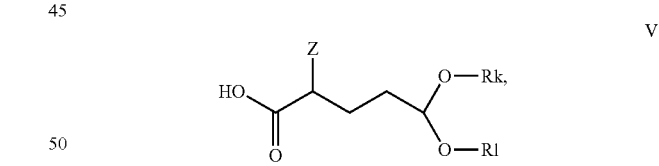

V wherein Rk and Rl are as defined for a compound of the formula II in claim 1 and above and Z is a protected amino group either of the formula NHProt* wherein Prot* is a protecting group that can be removed before or during the cleaving reaction under (iii/b) or further subsequently; or Z is a protected amino group of the formula N(Prot)$_2$ wherein each Prot is an amino protecting group that can be removed under conditions different to those of the cleaving reaction under in claim 5, or an activated derivative of said amino acid, with a compound of the formula VI,

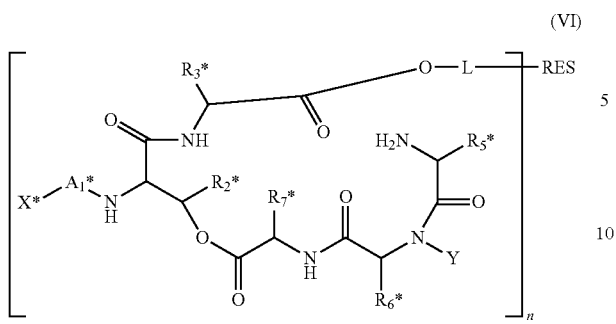

(VI)

wherein X*, A₁*, R₂*, R₃*, R₅*, R₆* and R₇* are as defined for a compound of the formula II in claim 1, L is a cleavable linker, RES is a solid resin, and n is a natural number not including 0.

7. The process according to claim 6, further comprising, for the synthesis of the compound of the formula VI, coupling an amino acid of the formula VII

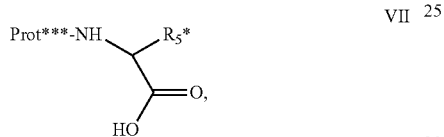

VII wherein R₅* is as defined for a compound of the formula II in claim 1 and Prot*** is an amino protecting group that can be cleaved off selectively without affecting other protecting groups present and with the product remaining on the resin, or a reactive derivative of said amino acid, with a compound of the formula VIII,

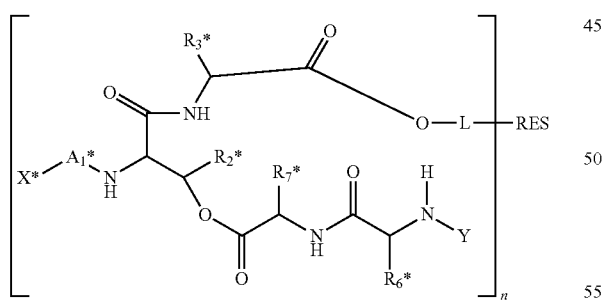

VIII wherein X*, A₁*, R₂*, R₃*, R₆* and R₇* are as defined for a compound of the formula II in claim 1, L is a cleavable linker, RES is a solid resin, and n is a natural number not including 0, and removing the protecting group Prot***.

8. The process according to claim 7, further comprising, for the synthesis of the compound of the formula VIII, coupling an amino acid of the formula IX,

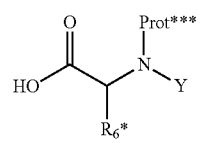

IX in which R₆* and Y are as defined for a compound of the formula II in claim 1 and Prot*** is an amino protecting group that can be cleaved off selectively without affecting other protecting groups present and with the product remaining on the resin, or a reactive derivative of said amino acid, with a compound of the formula X,

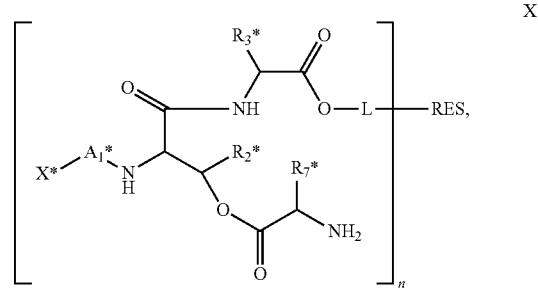

X wherein X*, A₁*, R₂*, R₃* and R₇* are as defined for a compound of the formula II in claim 1, L is a cleavable linker, RES is a solid resin, and n is a natural number not including 0, and removing the protecting group Prot***.

9. The process according to claim 8, further comprising, for the synthesis of a compound of the formula X, reacting an amino acid of the formula XI,

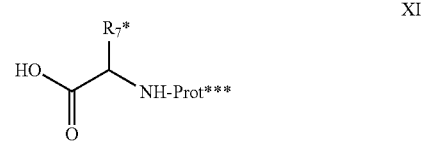

XI wherein Prot*** is an amino protecting group that can be cleaved off selectively without affecting other protecting groups present and with the product remaining on the resin, and R₇* is as defined for a compound of the formula II in claim 1, or a reactive derivative of said amino acid,
with the hydroxyl group of a compound of the formula XII,

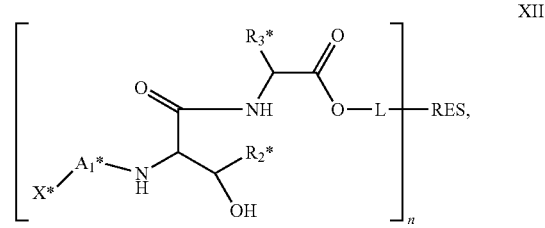

XII wherein X*, A₁*, R₂* and R₃* are as defined for a compound of the formula II in claim 1, L is a cleavable linker, RES is a solid resin, and n is a natural number not including 0;

and removing the protecting group Prot***.

10. The process according to claim 9, further comprising, for the synthesis of a compound of the formula XII, coupling a resin bound dipeptide symbolized by the formula XIII,

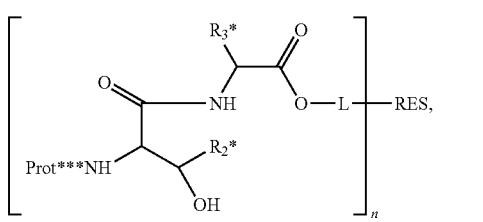

in which Prot**** is a protecting group that can be cleaved off selectively without affecting other protecting groups present in a compound of the formula II as defined above and with the product remaining on the resin, $R_2^*$ and $R_3^*$ are as defined for a compound of the formula II in claim 1, L is a cleavable linker, RES is a solid resin, and n is a natural number not including 0, after removal of the protecting group Prot**** via the thus obtainable free amino group, with an acid of the formula XIV,

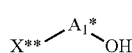

wherein X** is an amino protecting group or is X*, and wherein X* and $A_1^*$ are as defined for a compound of the formula II in claim 1, or a reactive derivative of said acid; and, if X is an amino protecting group, removing said amino protecting group X to yield the derivative of formula II wherein, instead of X*, H is present and coupling the resulting amino group with an acyl group X* using the corresponding acid X*—OH wherein X* is as defined for a compound of the formula II above, or a reactive derivative of said acid.

11. The process according to claim 10, further comprising, for the synthesis of a compound of the formula XIII, coupling a resin bound amino acid symbolized by the formula XV,

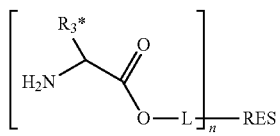

wherein $R_3^*$ is as defined for a compound of the formula II in claim 1, L is a cleavable linker, RES is a solid resin, and n is a natural number not including 0, with an amino acid of the formula XVI.

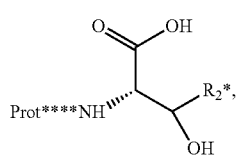

wherein Prot**** is a protecting group that can be cleaved off selectively without affecting other protecting groups present and with the product remaining on the resin, and $R_2^*$ is as defined for a compound of the formula II in claim 1, or a reactive derivative of said amino acid.

12. The process according to claim 1, where the symbols $A_1$, $R_2$, $R_3$, $R_5$, $R_6$, $R_7$, X and Y or the corresponding unprotected or protected moieties $R_2^*$, $R_3^*$, $R_5^*$, $R_6^*$, $R_7^*$, X* and Y3 are selected so that, in the resulting compound of the formula I, or a salt thereof, $A_1$ is the bivalent radical of L-glutamine bound via the carbonyl of its α-carboxyl group to the amino group at the right of $A_1$ in formula I and via its α-amino group to X, or is 2S-(2-hydroxy-3-phosphonooxy)-propionyl;

$R_2$ is methyl;

$R_3$ is isopropyl, isobutyl or benzyl;

$R_5$ is sec-butyl or benzyl;

$R_6$ is 4-hydroxybenzyl;

$R_7$ is isopropyl or sec-butyl;

X is acetyl or isobutyryl, or is absent if $A_1$ is 2S-(2-hydroxy-3-phosphonooxy)-propionyl and Y is methyl.

13. A process for converting a dehydrate of a compound of the formula I given in claim 1 or with the substituents as defined in claim 12, in each case obtained according to the process of claim 1, into the corresponding compound of the formula I, where the dehydrate has the formula XVIII,

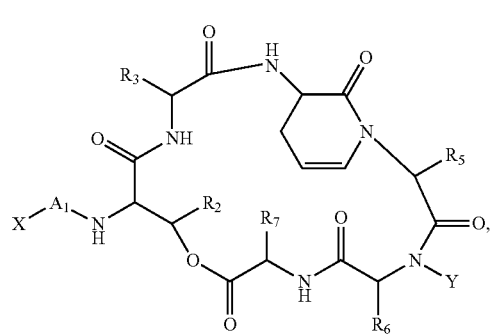

in which Y, X, $A_1$, $R_2$, $R_3$, $R_5$, $R_6$ and $R_7$ are as defined for a compound of the formula I in any one of claims 1 and 11;

and/or its corresponding hemiaminal analogue with a five-ring instead of the 3-amino-6-hydroxy-piperidin-2-one structure in formula I which may also be formed as byproduct and has the formula XIX, XIX
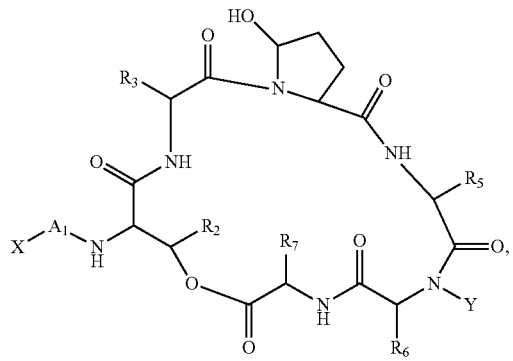

in which Y, X, $A_1$, $R_2$, $R_3$, $R_5$, $R_6$ and $R_7$ are as defined for a compound of the formula I in any one of claim 1, respectively;

or a process for shifting the equilibrium of a mixture of a compound of the formula I obtained according to the process of claim 1 and its corresponding dehydrate and/or hemiaminal in favor of the compound of the formula I, said process comprising using an aqueous acid as reactive solvent to drive the reaction.

14. A process for the synthesis of a compound of the formula V mentioned in claim 6, according to either (a) in the case of the synthesis of a compound of the formula V wherein Rk and Rl together form an unsubstituted or substituted lower alkylen bridge, the following reaction scheme, alternatively via the route (i) 1*→2*→3*, (ii) 1*→2*→4*→5*, or (iii) 1*→2*→3*→5*:

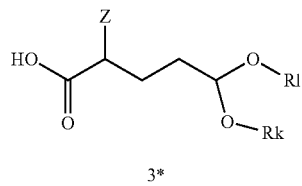

3*

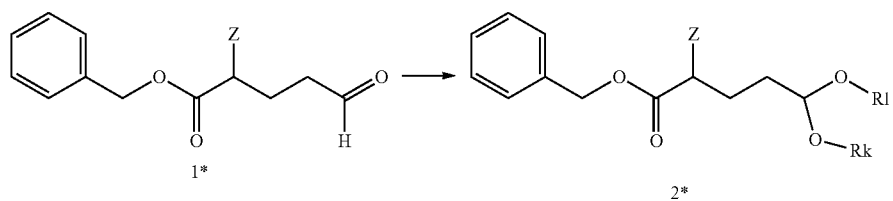

1*                 2*

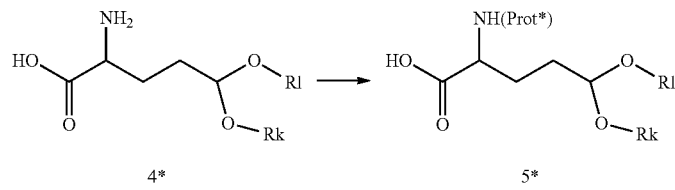

4*                 5* wherein Rk, Rl have the meanings just indicated and Z has the meanings mentioned in claim 6 for a compound of the formula V;

or (b) in the case of the synthesis of a compound of the formula V, wherein each of Rk and Rl is an unsubstituted or substituted alkyl moiety, according to the following reaction scheme:

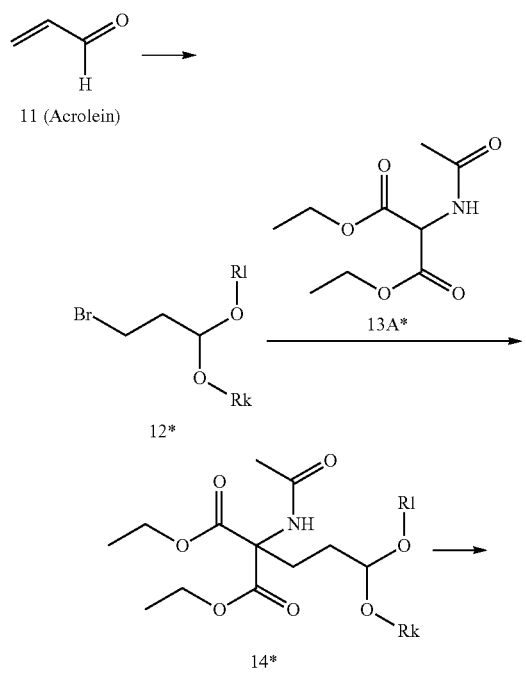

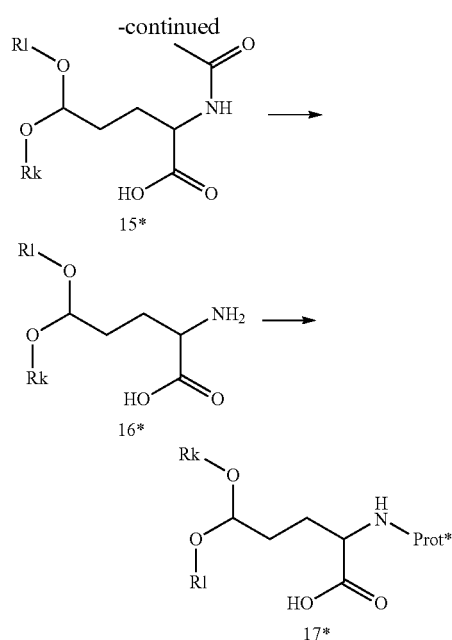

(wherein Rk, Rl have the meanings just indicated and Prot* has the meanings mentioned in claim 6 for a compound of the formula V.

15. The process according to claim 12, where the symbols $A_1$, $R_2$, $R_3$, $R_5$, $R_6$, $R_7$, X and Y or the corresponding unprotected or protected moieties $R_2^*$, $R_3^*$, $R_5^*$, $R_6^*$, $R_7^*$, $X^*$ and Y3 are selected so that, in the resulting compound of the formula I, or a salt thereof, $R_3$ is isobutyl;
$R_5$ is sec-butyl;
$R_7$ is sec-butyl.

* * * * *